(12) United States Patent
Apte et al.

(10) Patent No.: US 10,789,334 B2
(45) Date of Patent: *Sep. 29, 2020

(54) METHOD AND SYSTEM FOR MICROBIAL PHARMACOGENOMICS

(71) Applicant: PSOMAGEN, INC., Rockville, MD (US)

(72) Inventors: Zachary Apte, San Francisco, CA (US); Jessica Richman, San Francisco, CA (US); Daniel Almonacid, San Francisco, CA (US); Inti Pedroso, San Francisco, CA (US); Juan Ugalde, San Francisco, CA (US); Rodrigo Ortiz, San Francisco, CA (US)

(73) Assignee: PSOMAGEN, INC., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/649,497

(22) Filed: Jul. 13, 2017

(65) Prior Publication Data

US 2017/0308669 A1  Oct. 26, 2017

Related U.S. Application Data

(63) Continuation-in-part of application No. 15/606,743, filed on May 26, 2017, which is a continuation of application No. 14/919,614, filed on Oct. 21, 2015, now Pat. No. 9,703,929.

(60) Provisional application No. 62/066,369, filed on Oct. 21, 2014, provisional application No. 62/087,551, filed on Dec. 4, 2014, provisional application No. 62/092,999, filed on Dec. 17, 2014, provisional application No. 62/147,376, filed on Apr. 14, 2015, provisional application No. 62/147,212, filed on Apr. 14, 2015, provisional application No. 62/147,362, (Continued)

(51) Int. Cl.

| | | |
|---|---|---|
| *G01N 33/48* | (2006.01) | |
| *G06F 19/00* | (2018.01) | |
| *G16B 50/00* | (2019.01) | |
| *C12Q 1/6883* | (2018.01) | |
| *C12Q 1/689* | (2018.01) | |
| *G16H 40/63* | (2018.01) | |
| *G16H 40/67* | (2018.01) | |
| *G16H 50/50* | (2018.01) | |
| *G16H 50/20* | (2018.01) | |
| *G16H 10/40* | (2018.01) | |
| *G16H 20/40* | (2018.01) | |
| *G16H 20/10* | (2018.01) | |
| *G16B 20/00* | (2019.01) | |
| *G16B 50/30* | (2019.01) | |
| *G06G 7/58* | (2006.01) | |
| *G16B 40/20* | (2019.01) | |
| *G16B 50/20* | (2019.01) | |
| *G16B 30/10* | (2019.01) | |

(52) U.S. Cl.
CPC ......... *G06F 19/3418* (2013.01); *C12Q 1/689* (2013.01); *C12Q 1/6883* (2013.01); *G06F 19/30* (2013.01); *G16B 20/00* (2019.02); *G16B 50/00* (2019.02); *G16B 50/30* (2019.02); *G16H 10/40* (2018.01); *G16H 20/10* (2018.01); *G16H 20/40* (2018.01); *G16H 40/63* (2018.01); *G16H 40/67* (2018.01); *G16H 50/20* (2018.01); *G16H 50/50* (2018.01); *C12Q 2600/106* (2013.01); *C12Q 2600/118* (2013.01); *C12Q 2600/156* (2013.01); *G16B 30/10* (2019.02); *G16B 40/20* (2019.02); *G16B 50/20* (2019.02)

(58) Field of Classification Search
None
See application file for complete search history.

(56) References Cited

U.S. PATENT DOCUMENTS

| | | | |
|---|---|---|---|
| 6,033,864 A | 3/2000 | Braun et al. | |
| 6,309,643 B1 | 10/2001 | Braun et al. | |
| (Continued) | | | |

FOREIGN PATENT DOCUMENTS

| | | |
|---|---|---|
| CN | 105407728 | 3/2015 |
| EP | 2631240 | 8/2013 |
| (Continued) | | |

OTHER PUBLICATIONS

"K03100: lepB: signal peptidase I, " Kegg, Aug. 7, 2012 (Aug. 7, 2012), p. 1 of 1. Retrieved from the Internet: on Jun. 12, 2016 (Jun. 12, 2016).

"KEGG: Aminoacyl-tRNA biosynthesis—Reference pathway," Jul. 20, 2013 (Jul. 20, 2013). Retrieved from the internet: <http://web:archive.org/web/20130720015616/http:www.genome.jp/kegg-bin/show_pathway?map=map00970&show_description=show on Jun. 20, 2016 (Jun. 20, 2016).

(Continued)

*Primary Examiner* — Eric S DeJong
(74) *Attorney, Agent, or Firm* — Lex IP Meister, PLLC

(57) ABSTRACT

Embodiments of a method and system for microbial pharmacogenomics can include: a sample handling system operable to collect containers including biological samples from a set of users, the handling system including a sequencing system operable to determine microorganism sequences from the biological samples; a microbiome characterization system operable to: determine microbiome pharmacogenomics data based on the microorganism sequences, collect supplementary data associated with the antibiotics-associated condition for the set of users, and transform the supplementary data and features extracted from the microbiome pharmacogenomics data into a characterization model associated with the antibiotics-associated condition; and a treatment system operable to promote a treatment to the user for the antibiotics-associated condition based on characterizing user biological material with the characterization model in relation to the antibiotics-associated condition.

22 Claims, 13 Drawing Sheets

Related U.S. Application Data filed on Apr. 14, 2015, provisional application No. 62/146,855, filed on Apr. 13, 2015, provisional application No. 62/206,654, filed on Aug. 18, 2015, provisional application No. 62/361,943, filed on Jul. 13, 2016.

(56) References Cited

U.S. PATENT DOCUMENTS

| | | |
|---|---|---|
| 6,632,641 B1 | 10/2003 | Brennan et al. |
| 6,861,053 B1 | 3/2005 | Lin et al. |
| D521,843 S | 5/2006 | Hung |
| 7,048,906 B2 | 5/2006 | Lin et al. |
| 7,176,002 B2 | 2/2007 | Lao et al. |
| 8,478,544 B2 | 7/2013 | Colwell et al. |
| 8,598,203 B2 | 12/2013 | Tarcic et al. |
| 8,883,264 B2 | 11/2014 | Yang et al. |
| 9,028,841 B2 | 5/2015 | Henn et al. |
| 9,149,473 B2 | 10/2015 | Ecker et al. |
| 9,289,418 B2 | 3/2016 | Pimentel et al. |
| 9,433,651 B2 | 9/2016 | Jones et al. |
| 9,447,195 B2 | 9/2016 | Cordova et al. |
| 9,506,109 B2 | 11/2016 | Savelkoul et al. |
| 9,663,831 B2 | 5/2017 | Apte et al. |
| 9,700,586 B2 | 7/2017 | Bicalho et al. |
| 9,707,207 B2 | 7/2017 | Finegold |
| 9,710,606 B2 | 7/2017 | Apte et al. |
| 2002/0012926 A1 | 1/2002 | Quake et al. |
| 2003/0190314 A1 | 10/2003 | Campbell et al. |
| 2005/0196785 A1 | 9/2005 | Quake et al. |
| 2006/0073501 A1 | 4/2006 | Van Den Boom et al. |
| 2006/0089310 A1 | 4/2006 | Goldstein et al. |
| 2007/0134652 A1 | 6/2007 | Slepnev et al. |
| 2007/0259337 A1 | 11/2007 | Hully et al. |
| 2008/0131556 A1 | 6/2008 | De Simone et al. |
| 2010/0035232 A1 | 2/2010 | Ecker et al. |
| 2010/0129816 A1 | 5/2010 | Savelkoul et al. |
| 2010/0172874 A1 | 7/2010 | Turnbaugh et al. |
| 2011/0027219 A1 | 2/2011 | Tarcic et al. |
| 2011/0177976 A1 | 7/2011 | Gordon et al. |
| 2012/0045771 A1 | 2/2012 | Beier et al. |
| 2012/0129794 A1 | 5/2012 | Dowd et al. |
| 2012/0149584 A1 | 6/2012 | Olle et al. |
| 2012/0252775 A1 | 10/2012 | Calvillo et al. |
| 2013/0017999 A1 | 1/2013 | Fremont et al. |
| 2013/0045874 A1 | 2/2013 | Ehrlich |
| 2013/0108598 A1 | 5/2013 | Oresic et al. |
| 2013/0121968 A1 | 5/2013 | Quay |
| 2013/0184302 A1 | 7/2013 | Bortey et al. |
| 2014/0093478 A1 | 4/2014 | Turnbaugh et al. |
| 2014/0136120 A1 | 5/2014 | Colwell et al. |
| 2014/0179726 A1 | 6/2014 | Bajaj et al. |
| 2014/0199281 A1 | 7/2014 | Henn et al. |
| 2014/0315929 A1 | 10/2014 | Chiosis |
| 2014/0341853 A1 | 11/2014 | Hovanky |
| 2014/0363399 A1 | 12/2014 | Jones et al. |
| 2015/0050245 A1 | 2/2015 | Herman et al. |
| 2015/0211055 A1 | 7/2015 | Apte et al. |
| 2015/0211078 A1 | 7/2015 | Apte et al. |
| 2015/0213193 A1 | 7/2015 | Apte et al. |
| 2015/0374761 A1 | 12/2015 | Sadowsky et al. |
| 2016/0032363 A1 | 2/2016 | Stintzi et al. |
| 2016/0040216 A1 | 2/2016 | Akins et al. |
| 2016/0110515 A1 | 4/2016 | Apte et al. |
| 2016/0138089 A1 | 5/2016 | Harris et al. |
| 2016/0223553 A1 | 8/2016 | Sears et al. |
| 2016/0228003 A1 | 8/2016 | Apte et al. |
| 2016/0232312 A1 | 8/2016 | Apte et al. |
| 2016/0290132 A1 | 10/2016 | Knight et al. |
| 2017/0039347 A1 | 2/2017 | Apte et al. |
| 2017/0081707 A1 | 3/2017 | Dillon et al. |
| 2017/0107557 A1 | 4/2017 | Embree et al. |
| 2017/0262608 A1 | 9/2017 | Apte et al. |
| 2017/0268045 A1 | 9/2017 | Apte et al. |
| 2017/0268046 A1 | 9/2017 | Apte et al. |
| 2017/0270268 A1 | 9/2017 | Apte et al. |
| 2017/0270269 A1 | 9/2017 | Apte et al. |
| 2017/0270270 A1 | 9/2017 | Apte et al. |
| 2017/0270271 A1 | 9/2017 | Apte et al. |
| 2017/0270272 A1 | 9/2017 | Apte et al. |
| 2017/0286619 A1 | 10/2017 | Apte et al. |
| 2017/0286620 A1 | 10/2017 | Apte et al. |
| 2017/0327864 A1 | 11/2017 | Apte et al. |
| 2017/0344719 A1 | 11/2017 | Apte et al. |
| 2018/0070827 A1 | 3/2018 | Apte et al. |
| 2019/0085396 A1 | 3/2019 | Apte et al. |

FOREIGN PATENT DOCUMENTS

| | | |
|---|---|---|
| EP | 2994756 | 3/2016 |
| WO | 039234 | 5/2003 |
| WO | 113066 | 9/2011 |
| WO | 050513 | 4/2012 |
| WO | 121298 | 8/2014 |
| WO | 138999 | 9/2014 |
| WO | 144092 | 9/2014 |
| WO | 145958 | 9/2014 |
| WO | 013214 | 1/2015 |
| WO | 085326 | 6/2015 |
| WO | 095241 | 6/2015 |
| WO | 103165 | 7/2015 |
| WO | 112352 | 7/2015 |
| WO | 170979 | 11/2015 |
| WO | 2015/095241 A4 | 12/2015 |
| WO | 2016/065075 A1 | 4/2016 |
| WO | 2016/086308 A1 | 6/2016 |
| WO | 138337 | 9/2016 |
| WO | 172643 | 10/2016 |
| WO | 044902 | 3/2017 |

OTHER PUBLICATIONS

Avila, Maria et al., The Oral Microbiota: Living with a Permanent Guest, DNA and Cell Biology, Nov. 8, 2009, vol. 28, No. 8.

Carroll et al. "Alterations in composition and diversity of the intestinal microbiota in patients with diarrhea-predominant irritable bowel syndrome," Feb. 20, 2012 (Feb. 20, 2012), vol. 24, pp. 1-19 [Original pp. 5215-5230] entire document.

Cho et al. "The Human Microbiome: at the Interface of Health and Disease," Nature Reviews Genetics, Apr. 1, 2012 (Apr. 1, 2012), vol. 13, pp. 260-270.

DeWhirst, Floyd et al., The Human Oral Microbiome, Journal of Bacteriology, Oct. 2010, vol. 192, No. 19, pp. 5002-5017.

Evans, Morgan, Prosthetic valve endocarditis due to Neisseria elongata subsp. elongata in a patient with Klinefelter's syndrome, Journal of Medical Microbiology, Jun. 1, 2007, vol. 56, No. 6, pp. 860-862.

Greenblum et al. "Metagenomic Systems Biology of the Human Gut Microbiome Reveals Topological Shifts Associated with Obesity and Inflammatory Bowel Disease," Proceeding of the National Academy of Sciences, Dec. 19, 2011 (Dec. 19, 2011), vol. 109, pp. 594-599.

Kanehisa et al. "KEGG: Kyoto encyclopedia of genes and genomes,"Nucleic Acids Research, Jan. 1, 2000 (Jan. 1, 2000), vol. 28, No. 1, pp. 27-30.

Mak et al. "MetaboLyzer: A Novel Statistical Workflow for Analyzing Post Processed LC/MS Metabolomics Data," Anal Chem, Jan. 7, 2014 (Jan. 7, 2014 ), vol. 86, pp. 506-513.

Morgan et al. "Dysfunction of the intestinal microbiome in inflammatory bowel disease and treatment," Genome Biol. Apr. 16, 2012 (Apr. 16, 2012), vol. 13(9):R79, pp. 1-18. entire document.

Mutulu et al. "A Compositional Look at the Human Gastrointestinal Microbiome and Immune Activation Parameters in HIV Infected Subjects," PLoS Pathogens, Feb. 20, 2014 (Feb. 20, 2014), vol. 10, pp. 1-18.

Nakayama et al. "Aberrant Structures of Fecal Bacterial Community in Allergic Infants Profiled by 16S rRNA Gene Pyrosequencing," FEMS Immunology & Medical Microbiology, Dec. 1, 2011 (Dec. 1, 2011), vol. 63, pp. 397-406.

(56) References Cited

OTHER PUBLICATIONS

Ponnusamy et al. "Microbial community and metabolomic comparison of irritable bowel syndrome faeces," Feb. 17, 2011 (Feb. 17, 2011), vol. 60, pp. 817-827. entire document.
International Application No. PCT/US2015/056767, International Preliminary Report on Patentability dated May 4, 2017, 9 pages.
International Application No. PCT/US2015/056767, International Search Report and Written Opinion dated Jan. 11, 2016, 10 pages.
International Application No. PCT/US2017/042015, International Search Report and Written Opinion dated Sep. 26, 2017, 12 pages.
U.S. Appl. No. 14/919,614, Non-Final Office Action dated Jul. 14, 2016, 10 pages.
U.S. Appl. No. 14/919,614, Notice of Allowance dated May 19, 2017, 10 pages.
U.S. Appl. No. 15/606,743, Non Final Office Action dated Dec. 19, 2017, 10 pages.
U.S. Appl. No. 15/606,743, Notice of Allowance dated Sep. 20, 2018, 5 pages.
Canadian Application No. 2,962,466, Examination Report dated Mar. 23, 2018, 4 pages.
European Application No. 15852829.9, Extended European Search Report dated May 14, 2018, 8 pages.
International Application No. PCT/US2017/042015, International Preliminary Report on Patentability dated Jan. 24, 2019, 11 pages.
Kinross, et al., "Gut Microbiome-host Interactions in Health and Disease", Genome Medicine, vol. 3, No. 14, 2011, pp. 1-12.
Morgan, et al., "Biodiversity and Functional Genomics in the Human Microbiome", Trends Genet, vol. 29, No. 1, Jan. 2013, pp. 51-58.
U.S. Appl. No. 15/606,824, Final Office Action dated Sep. 20, 2018, 8 pages.
U.S. Appl. No. 15/606,824, Non-Final Office Action dated Jan. 16, 2018, 10 pages.
U.S. Appl. No. 15/606,874, Final Office Action dated Aug. 31, 2018, 8 pages.
U.S. Appl. No. 15/606,874, Non-Final Office Action dated Feb. 9, 2018, 10 pages.
U.S. Appl. No. 15/606,874, Notice of Allowance dated Jan. 17, 2019, 5 pages.
U.S. Appl. No. 15/606,909, Final Office Action dated Sep. 20, 2018, 8 pages.
U.S. Appl. No. 15/606,909, Non-Final Office Action dated Mar. 9, 2018, 10 pages.
U.S. Appl. No. 15/606,909, Notice of Allowance mailed dated Feb. 20, 2019, 5 pages.
U.S. Appl. No. 15/606,943, Final Office Action mailed dated Nov. 1, 2018, 7 pages.
U.S. Appl. No. 15/606,943, Non-Final Office Action dated Apr. 10, 2018, 10 pages.
U.S. Appl. No. 15/606,943, Notice of Allowance dated Mar. 8, 2019, 5 pages.
U.S. Appl. No. 15/606,975, Final Office Action dated Jun. 14, 2018, 8 pages.
U.S. Appl. No. 15/606,975, Non-Final Office Action dated Sep. 25, 2017, 10 pages.
U.S. Appl. No. 15/606,975, Notice of Allowance dated Oct. 19, 2018, 5 pages.
U.S. Appl. No. 15/621,144, Final Office Action dated Nov. 1, 2018, 7 pages.
U.S. Appl. No. 15/621,144, Non-Final Office Action dated Apr. 10, 2018, 10 pages.
U.S. Appl. No. 15/621,144, Notice of Allowance dated Mar. 8, 2019, 6 pages.
U.S. Appl. No. 15/621,152, Final Office Action dated Nov. 1, 2018, 7 pages.
U.S. Appl. No. 15/621,152, Non-Final Office Action dated Apr. 10, 2018, 10 pages.
U.S. Appl. No. 15/621,152, Notice of Allowance dated Mar. 8, 2019, 6 pages.

METHOD AND SYSTEM FOR MICROBIAL PHARMACOGENOMICS

CROSS-REFERENCE TO RELATED APPLICATIONS

This application is a continuation-in-part of U.S. patent application Ser. No. 15/606,743, filed 26 May 2017, which is a continuation of U.S. patent application Ser. No. 14/919,614, filed 21 Oct. 2015, which claims the benefit of U.S. Provisional Application Ser. No. 62/066,369, filed 21 Oct. 2014, U.S. Provisional Application Ser. No. 62/087,551, filed 4 Dec. 2014, U.S. Provisional Application Ser. No. 62/092,999, filed 17 Dec. 2014, U.S. Provisional Application Ser. No. 62/147,376, filed 14 Apr. 2015, U.S. Provisional Application Ser. No. 62/147,212, filed 14 Apr. 2015, U.S. Provisional Application Ser. No. 62/147,362, filed 14 Apr. 2015, U.S. Provisional Application Ser. No. 62/146,855, filed 13 Apr. 2015, and U.S. Provisional Application Ser. No. 62/206,654, filed 18 Aug. 2015, which are each incorporated in its entirety herein by this reference.

This application additionally claims the benefit of U.S. Provisional Application Ser. No. 62/361,943, filed 13 Jul. 2016, which is incorporated in its entirety by this reference.

TECHNICAL FIELD

This invention relates generally to the field of microbiology and more specifically to a new and useful method and system for microbial pharmacogenomics in the field of microbiology.

BACKGROUND

A microbiome is an ecological community of commensal, symbiotic, and pathogenic microorganisms that are associated with an organism. The human microbiome includes as many microbial cells as human cells present in the entire human body, but characterization of the human microbiome is still in nascent stages due to limitations in sample processing techniques, genetic analysis techniques, and resources for processing large amounts of data. Nonetheless, the microbiome is suspected to play at least a partial role in a number of health/disease-related states (e.g., preparation for childbirth, diabetes, autoimmune disorders, gastrointestinal disorders, rheumatoid disorders, neurological disorders, etc.). Given the profound implications of the microbiome in affecting a subject's health, efforts related to the characterization of the microbiome, the generation of insights from the characterization, and the generation of therapeutics configured to rectify states of dysbiosis should be pursued. Current methods and systems for analyzing the microbiomes of humans and providing therapeutic measures based on gained insights have, however, left many questions unanswered. In particular, methods for characterizing certain health conditions and therapies (e.g., probiotic/prebiotic therapies, fecal microbiota transplantation, etc.) tailored to specific subjects based upon microbiome composition, functional features and/or pharmacogenomics features have not been viable due to limitations in current technologies.

As such, there is a need in the field of microbiology for a new and useful method and system for microbial pharmacogenomics in an individualized and population-wide manner. This technology creates such a new and useful method and system.

DESCRIPTION OF THE EMBODIMENTS

The following description of the embodiments of the invention is not intended to limit the invention to these embodiments, but rather to enable any person skilled in the art to make and use this invention.

1. Overview

Figure 2:
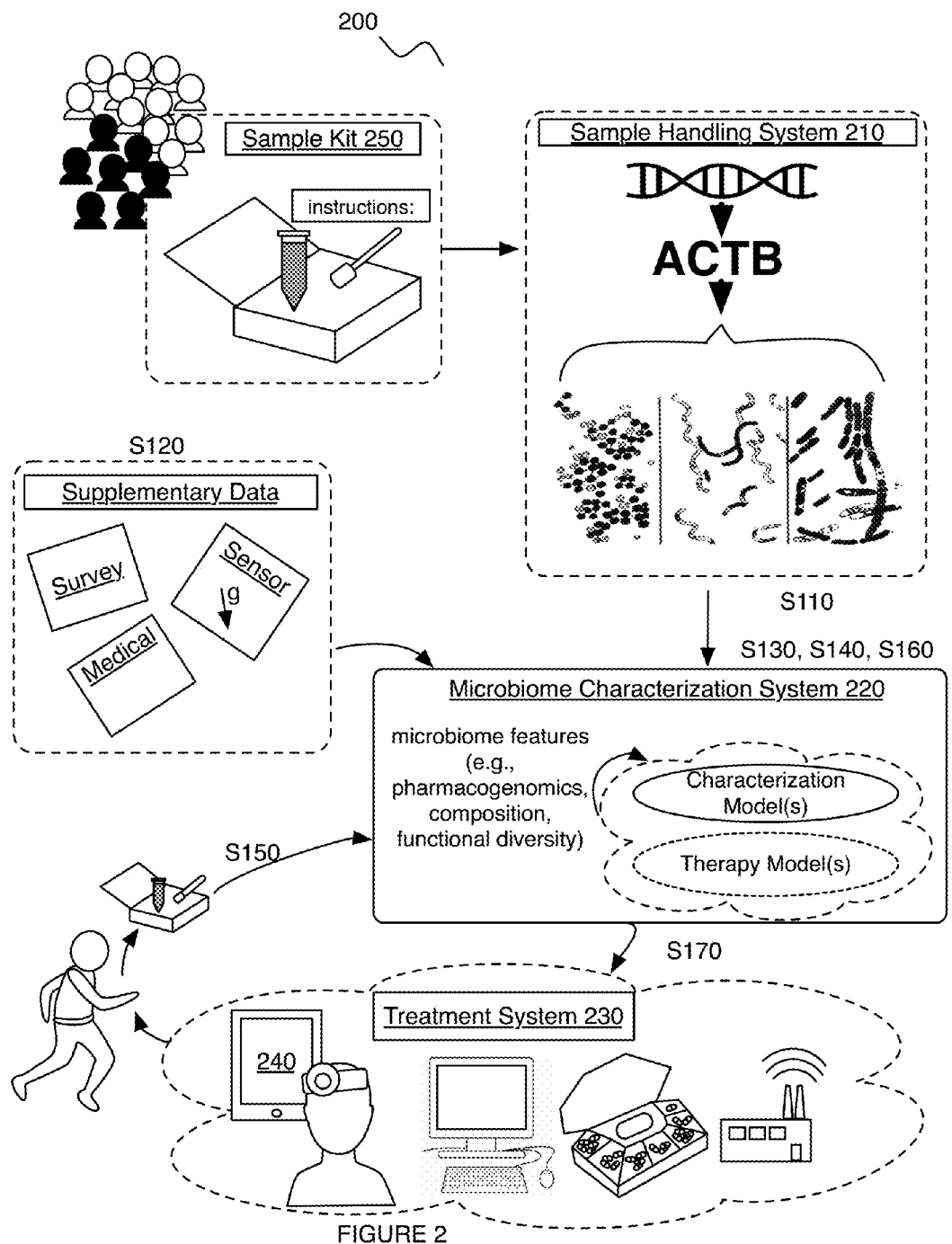
FIG. 2 depicts variations of embodiments of a system and method for microbial pharmacogenomics.

As shown in FIG. 2, embodiments of a system 200 for characterizing (e.g., evaluating) an antibiotics-associated condition in relation to a user (e.g., a human subject, patient, animal subject, environmental ecosystem, care provider, etc.) can include one or more of: a handling system 210 (e.g., a sample handling system) operable to collect containers including biological samples (e.g., biological material such as nucleic acid material) from a set of users, the handling system 210 including a sequencing system (e.g., sequencer system) operable to determine microorganism sequences from the biological samples; a microbiome characterization system 220 operable to: determine microbiome pharmacogenomics data (and/or at least one of microbiome composition data and microbiome functional diversity data) based on the microorganism sequences, collect supplementary data associated with the antibiotics-associated condition for the set of users, and transform the supplementary data and features extracted from the microbiome pharmacogenomics data (and/or the at least one of the microbiome composition data and the microbiome functional diversity data) into a characterization model associated with the antibiotics-associated condition; and a treatment system 230 (e.g., therapy system) operable to promote a treatment (e.g., therapy) to the user for the antibiotics-associated condition (e.g., where the treatment is operable to modulate a user microbiome composition for improving a state of the antibiotics-associated condition, etc.) based on characterizing user biological material with the characterization model in relation to the antibiotics-associated condition.

The system 200 and method 100 can function to characterize and/or diagnose users (e.g., using characterization models for a clinical diagnostic, for a companion diagnostic, etc.) according to microbiome datasets associated with one or more antibiotics-associated conditions. The system 200 and method 100 can additionally or alternatively function to promote (e.g., provide) treatments such as therapeutic measures to users and/or perform any suitable function. Variations of the system 200 and/or method 100 can be used to generate and/or provide personalized antibiotic regimens in an expedited and efficient manner in comparison to current standards of antibiotics-based treatments. Variations of the system 200 and/or method 100 can further facilitate monitoring and/or adjusting of such therapies provided to a subject, for instance, through reception, processing, and analysis of additional samples from a subject throughout the course of therapy.

The system 200 and method 100 can preferably generate and promote characterizations and/or therapies for antibiotics-associated conditions (e.g., antibiotics-treatable conditions), which can include any one or more of: symptoms, causes, diseases, disorders, microbiome pharmacogenomics profiles (e.g., describing resistance and/or susceptibility to antibiotics for an antibiotics-treatable condition) and/or any other suitable aspects associated with antibiotics-associated conditions. Antibiotics-associated conditions can include any one or more of: gonorrhea, urinary tract infection, trichomoniasis, acne, appendicitis, atrial septal defect, ureterocele, urethral syndrome, urethritis, tuberculosis, bacterial arthritis, bacterial vaginosis, vertigo, balance disorder, pressure ulcer, bursitis, bronchitis, syphilis, tonsillitis, pharyngitis, sepsis, pyelonephritis, ear infections, hearing loss, peritonitis, pericarditis, pelvic inflammatory disease, meningitis, laryngitis, strep throat, sinus infections, other sexually transmitted diseases, other skin-related conditions, other ear-related conditions, other mouth-related conditions, other bacterially induced infections, and/or any other suitable antibiotics-associated conditions.

One or more instances of the method 100 and/or processes described herein can be performed asynchronously (e.g., sequentially), concurrently (e.g., in parallel; concurrently on different threads for parallel computing to improve sample processing and/or computational processing for determining and/or providing characterizations and/or therapies for antibiotics-associated conditions; etc.), in temporal relation to a trigger event, and/or in any other suitable order at any suitable time and frequency by and/or using one or more instances of the system 200, components, and/or entities described herein. However, the method 100 and/or system 200 can be configured in any suitable manner.

2. Benefits.

Microbiome analysis can enable accurate and efficient characterization and/or therapy provision for antibiotics-associated conditions caused by and/or otherwise associated with microorganisms. The technology can overcome several challenges faced by conventional approaches in characterizing and/or promoting therapies for antibiotics-associated conditions. First, conventional approaches can require patients to visit one or more care providers to receive a characterization and/or a therapy recommendation for an antibiotic-associated condition, which can amount to inefficiencies and health-risks associated with the amount of time elapsed before diagnosis and/or treatment. Second, conventional genetic sequencing and analysis technologies for human genome sequencing can be incompatible and/or inefficient when applied to the microbiome (e.g., where the human microbiome can include over 10 times more microbial cells than human cells; where optimal sample processing techniques can differ; where sequence reference databases can differ; where microbiome characterization can include accounting for the different microbiome pharmacogenomics profiles across different populations and/or individuals; where different approaches can differ for microbiome pharmacogenomics analysis versus human genome pharmacogenomics analysis; where the microbiome can vary across different body regions of the user; etc.). Third, the onset of sequencing technologies (e.g., next-generation sequencing) has given rise to technological issues (e.g., data processing issues, information display issues, microbiome analysis issues, therapy prediction issues, therapy provision issues, etc.) that would not exist but for the unprecedented advances in speed and data generation associated with sequencing genetic material. Examples of the system 200 and the method 100 can confer technologically-rooted solutions to at least the challenges described above.

First, the technology can confer improvements in computer-related technology (e.g., modeling associated with determining personalized characterizations and/or treatments for antibiotics-associated conditions; microbiome pharmacogenomics computational analysis; computational processing associated with biological sample processing; etc.) by facilitating computer performance of functions not previously performable. For example, the technology can computationally generate microbiome characterizations and/or recommended therapies for antibiotics-associated conditions based on microbiome pharmacogenomics data derived from techniques (e.g., leveraging microorganism reference sequence databases such as the Genome Reference Consortium) that are recently viable due to advances in sample processing techniques and sequencing technology.

Second, the technology can confer improvements in processing speed, microbiome characterization accuracy, microbiome-related therapy determination and promotion, and/or other suitable aspects in relation to antibiotics-associated conditions. The technology can generate and apply feature-selection rules (e.g., microbiome pharmacogenomics feature-selection rules; antibiotics-associated feature-selection rules) to select an optimized subset of features (e.g., microbiome pharmacogenomics features, microbiome composition features, microbiome functional diversity features, etc.) out of a vast potential pool of features (e.g., extractable from the plethora of microbiome data) for generating and/or applying characterization models and/or therapy models (e.g., an antibiotic therapy model). The potential size of microbiomes (e.g., human microbiomes, animal microbiomes, etc.) can translate into a plethora of data, giving rise to questions of how to process and analyze the vast array of data to generate actionable microbiome insights in relation to antibiotics-associated conditions. However, the feature-selection rules and/or other suitable computer-implementable rules can enable shorter generation and execution times (e.g., for generating and/or applying decision tree models), model simplification facilitating efficient interpretation of results, reduction in overfitting, improvements in data sources (e.g., for collecting and processing microbiome datasets such as microbiome pharmacogenomics datasets, microbiome composition datasets, microbiome functional diversity datasets, etc.), improvements in identifying and presenting antibiotics-associated condition insights in relation to the microbiome (e.g., through collecting and processing an increasing amount of data associated with an increasing number of users to improve predictive power of the technology), improvements in data storage and retrieval (e.g., storing specific models, microorganism sequences, features, and/or other suitable data in association with a user and/or set of users to improve delivery of personalized characterizations and/or treatments, etc.), and other suitable improvements to facilitate rapid determination of characterizations and/or therapies.

Third, the technology can transform entities (e.g., users, biological samples, treatment systems including medical devices, etc.) into different states or things. For example, the system 200 and/or method 100 can identify therapies to promote to a patient to modify a microbiome pharmacogenomics profile, microbiome composition and/or microbiome functional diversity to prevent and/or ameliorate antibiotics-associated conditions, thereby transforming the microbiome and/or health of the patient. In another example, the technology can transform biological samples (e.g., through fragmentation, multiplex amplification, sequencing, etc.) received by patients into microbiome datasets, which can subsequently be transformed into features correlated with antibiotics-associated conditions, in order to generate characterization models and/or therapy models. In another example, the technology can control treatment systems to promote therapies (e.g., by generating control instructions for the treatment system to execute), thereby transforming the treatment system. In another example, the improvements in computer-related technology can drive transformations in the biological sample processing approaches, such as selecting a subset of primers compatible with genetic targets associated identified to correspond to microbiome pharmacogenomics features (e.g., mutations associated with antibiotic resistance or susceptibility), microbiome composition features and/or microbiome functional diversity features associated with antibiotics-associated conditions.

Fourth, the technology can amount to an inventive distribution of functionality across a network including a sample handling system, microbiome characterization system, and a plurality of users, where the sample handling system can handle substantially concurrent processing of biological samples (e.g., in a multiplex manner) from the plurality of users, which can be leveraged by the microbiome characterization system in generating personalized characterizations and/or therapies (e.g., customized to the user's microbiome such as the microbiome pharmacogenomics profile of the user, medical history, demographics, behaviors, preferences, etc.) for antibiotics-associated conditions.

Fifth, the technology can improve the technical fields of at least computational modeling of antibiotics-associated conditions in relation to microbiome digital medicine, digital medicine generally, genetic sequencing, and/or other relevant fields. Sixth, the technology can leverage specialized computing devices (e.g., devices associated with the sample handling system, such as sequencing systems; microbiome characterization systems; treatment systems; etc.) in determining and processing microbiome datasets for characterizing and/or determining therapies for antibiotics-associated conditions. The technology can, however, provide any other suitable benefit(s) in the context of using non-generalized computer systems for microbiome characterization and/or modulation.

3. System.

The handling system 210 of the system 200 can function to receive and process (e.g., fragment, amplify, sequence, etc.) biological samples. The handling system 210 can additionally or alternatively function to provide and/or collect sample kits 250 (e.g., including containers configured for receiving biological material, instructions for users to guide a self-sampling process, etc.) for a plurality of users (e.g., in response to a purchase order for a sample kit 250), such as through a mail delivery system and/or other suitable process. In examples, the sample kits 250 can include materials and associated instructions for a user to collect a sample (e.g., through cotton tip swabs; aspiration of fluids; biopsy; etc.) from one or more collection sites. Collection sites can be associated with one or more of: the female genitals, the male genitals, the rectum, the gut, the skin, the mouth, the nose, any mucous membrane, and/or any other suitable sample providing site (e.g., blood, sweat, urine, feces, semen, vaginal discharges, tears, tissue samples, interstitial fluid, other body fluid, etc.). The handling system 210 can additionally or alternatively include a library preparation system operable to automatically prepare biological samples (e.g., fragment and/or amplify using primers compatible with nucleic acid sequences associated with the antibiotics-associated condition, such as in a multiplex manner, etc.) to be sequenced by a sequencing system (e.g., a next generation sequencing platform); and/or any suitable components. However, the handling system 210 and associated components can be configured in any suitable manner.

The microbiome characterization system 220 of the system 200 can function to determine and/or analyze microbiome datasets and/or supplementary datasets for characterizing and/or determining therapies for antibiotics-associated conditions. In a variation, the microbiome characterization system 220 can obtain and/or apply computer-implemented rules (e.g., feature selection rules; model generation rules; user preference rules; data storage, retrieval, and/or display rules; microorganism sequence generation rules; sequence alignment rules; and/or any other suitable rules). However, the microbiome characterization system 220 can be configured in any suitable manner.

The treatment system 230 of the system 200 functions to promote one or more treatments to a user (e.g., a subject; a care provider facilitating provision of the treatment; etc.) for treating an antibiotics-associated condition (e.g., reducing the risk of the condition; modifying a microbiome pharmacogenomics profile of a user towards a state susceptible to treatments for an antibiotics-treatable condition, etc.). The treatment system 230 can include any one or more of: a communications system (e.g., to communicate treatment recommendations, such as through an interface 240, through notifying a care provider to recommend and/or provide the treatment; to enable telemedicine; etc.), an application executable on a user device (e.g., an antibiotics-associated condition application for promoting treatments; a medication reminder application; an application operable to communicate with an automatic medication dispenser; etc.), antibiotics-associated therapies such as antibiotics (e.g., type, dosage, medication schedule etc.), supplementary medical devices (e.g., medication dispensers; medication devices including antibiotics, such as antibiotic applicators for topical delivery, biodegradable antibiotic delivery systems, non-biodegradable antibiotic delivery systems, antibiotic delivery agents, nanoparticle delivery systems, scaffold delivery systems, bead delivery systems, controlled-release devices, elution devices, and/or other suitable drug delivery devices; diagnostic devices for antibiotics-associated conditions; etc.), user devices (e.g., including biometric sensors), and/or any other suitable component. One or more treatment systems 230 are preferably controllable by the microbiome characterization system 220. For example, the microbiome characterization system 220 can generate control instructions and/or notifications to transmit to the treatment system 230 for activating and/or otherwise operating the treatment system 230 in promoting the therapy. However, the treatment system 230 can be configured in any other manner.

Figure 9:
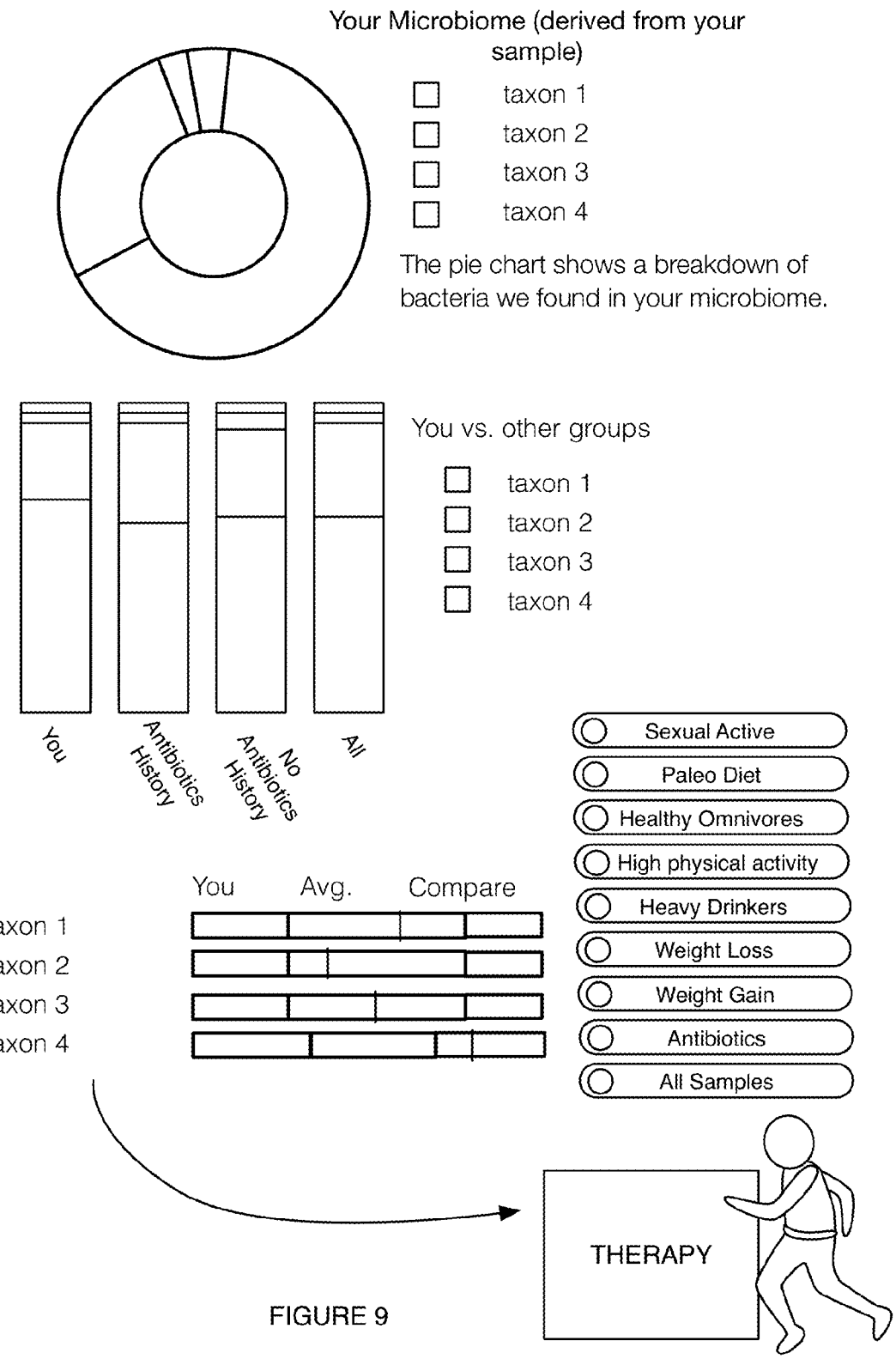
FIG. 9 depicts a variation of notification provision in an embodiment of a method for microbial pharmacogenomics.
Figure 10:
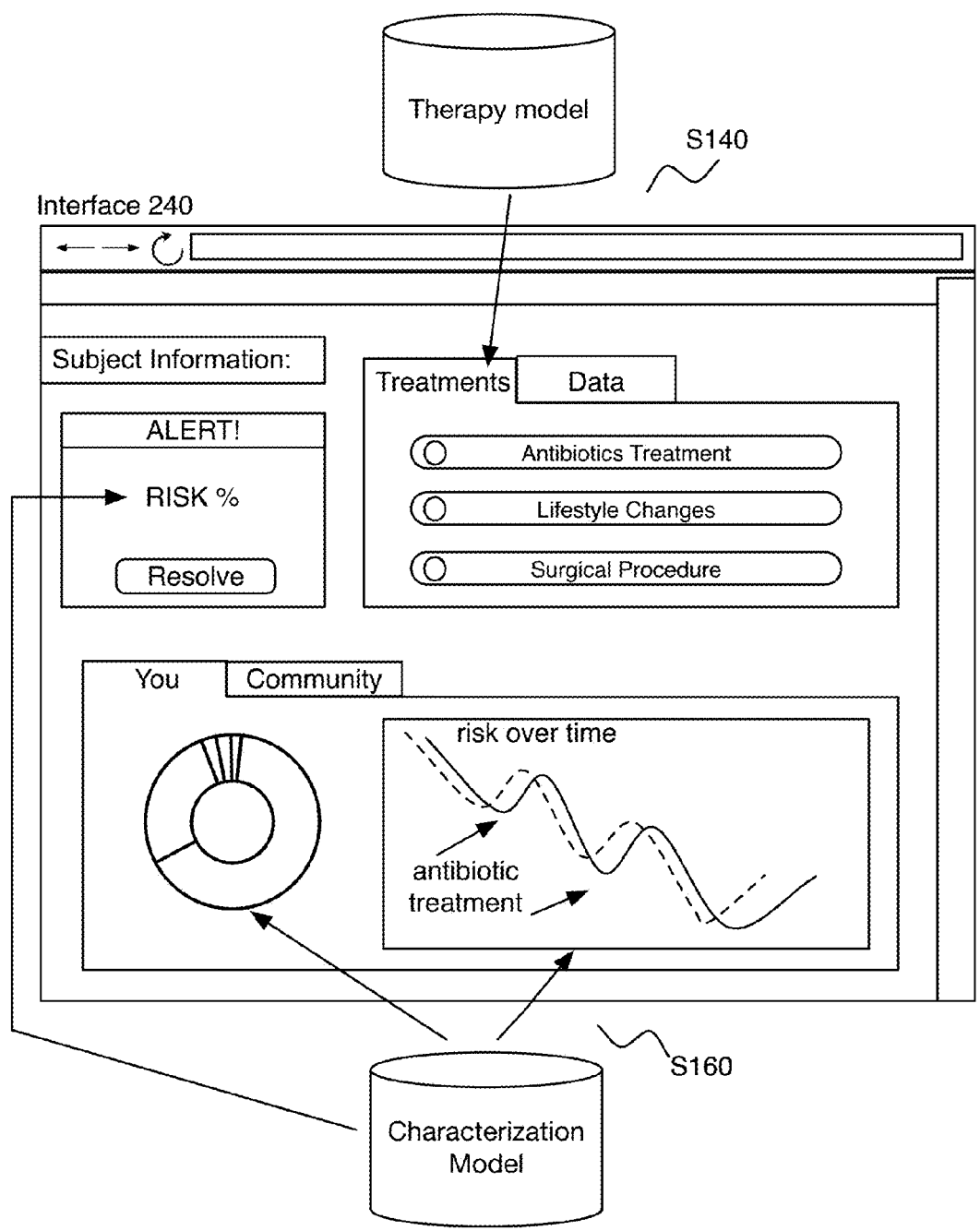
FIG. 10 depicts a variation of an interface for providing antibiotic-related information in an embodiment of a method for microbial pharmacogenomics.
Figure 11:
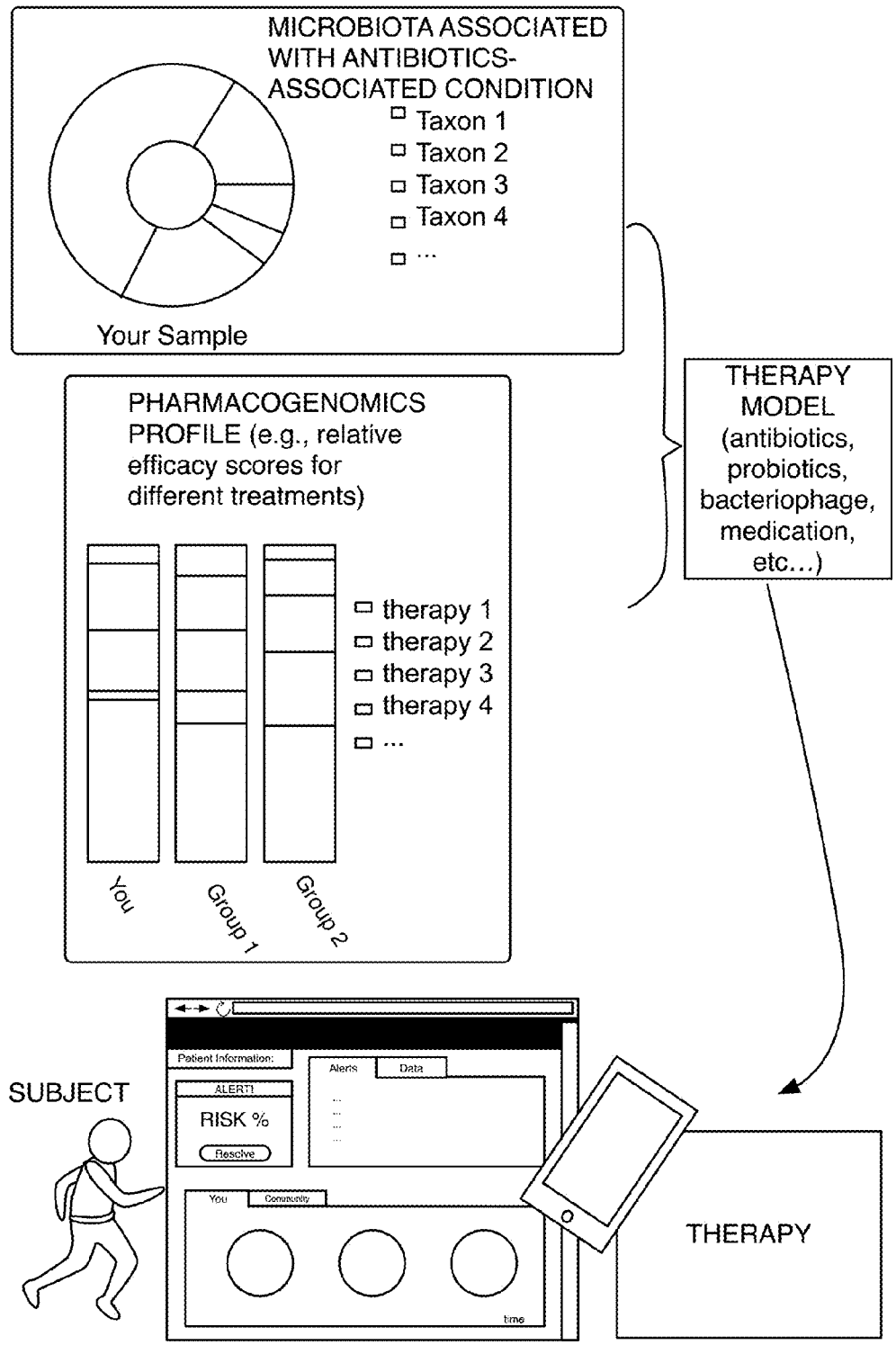
FIG. 11 depicts variations of notification provision in an embodiment of a method for microbial pharmacogenomics.

As shown in FIG. 10, the system 200 can additionally or alternatively include an interface 240 that can function to improve presentation of antibiotics-related information (e.g., characterizations of antibiotics-associated conditions; therapy recommendations; comparisons to other users; evaluations of treatments in relation to microbiome pharmacogenomics profile, as shown in FIG. 11; microbiome composition, as shown in FIG. 9; microbiome functional diversity; etc.). In another example, the interface 240 can present antibiotics-related information including a microbiome composition (e.g., taxonomic groups), functional diversity (e.g., relative abundance of genes associated with function correlated with antibiotics-associated conditions, etc.), and/or risk of one or more antibiotics-associated conditions for the user, such as relative to a user group sharing a demographic characteristic (e.g., patients sharing conditions, smokers, exercisers, users on different dietary regimens, consumers of probiotics, antibiotic users, groups undergoing particular therapies, etc.). In another example, the interface 240 can be operable to present antibiotics-related information including a change in the microbiome pharmacogenomics profile (and/or microbiome composition, microbiome functional diversity, etc.) over time in relation to the treatment and the antibiotics-associated condition. In a specific example, the interface can be operable to improve display of antibiotics-related information associated with the antibiotics-treatable condition and derived based on a comparison between a user microbiome pharmacogenomics profile for the user relative a user group sharing a demographic characteristic. In another specific example, the interface's display of antibiotics-related information can be improved through selection (e.g., based on components of the characterization satisfying a threshold condition; a user microbiome pharmacogenomics profile matching a reference profile beyond a threshold similarity; an antibiotics-associated condition risk exceeding a threshold; other trigger events; etc.) and presentation of a subset of antibiotics-related information (e.g., highlighting and/or otherwise emphasizing a subset of antibiotics-related information). However, the interface 240 can display any suitable information and can be configured in any suitable manner.

The system 200 and/or components of the system 200 can entirely or partially be executed by, hosted on, communicate with, and/or otherwise include: a remote computing system (e.g., a server, at least one networked computing system, stateless, stateful), a local computing system, databases (e.g., user database, microbiome dataset database, antibiotics-associated condition database, treatment database, etc.), a user device (e.g., a user smart phone, computer, laptop, supplementary medical device, wearable medical device, care provider device, etc.), and/or any suitable component. For example, the system 200 can include a computing system operable to communicate with the handling system 210 (e.g., a next generation sequencing platform of the handling system 210) to perform suitable portions of the method 100, such as determining microbiome pharmacogenomics data. While the components of the system 200 are generally described as distinct components, they can be physically and/or logically integrated in any manner. For example, a smartphone application can partially or fully implement the microbiome characterization system 220 (e.g., apply a characterization model to generate a characterization of antibiotic-associated conditions in real-time; sequence biological samples; process microorganism sequences; extract features from microbiome datasets; etc.) and the treatment system 230 (e.g., communicate with a calendar application of the smartphone to notify the user to take antibiotics according to the parameters determined by the antibiotic therapy model, etc.). Additionally or alternatively, the functionality of the system 200 can be distributed in any suitable manner amongst any suitable system components. However, the components of the system 200 can be configured in any suitable manner.

4. Method

Figure 1A:
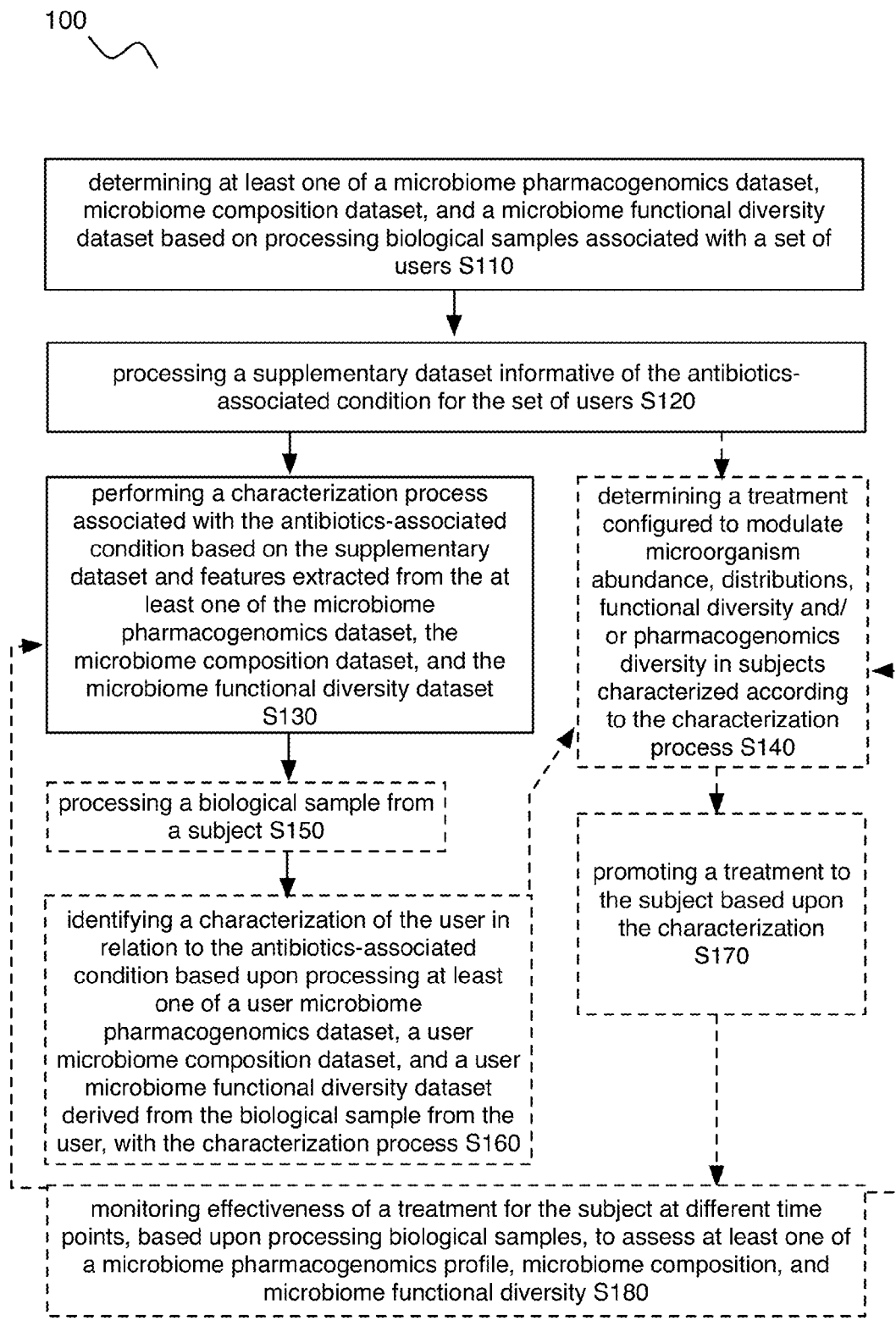
FIGS. 1A-1B depict flowchart representations of variations of embodiments of a method for microbial pharmacogenomics.
Figure 1B:
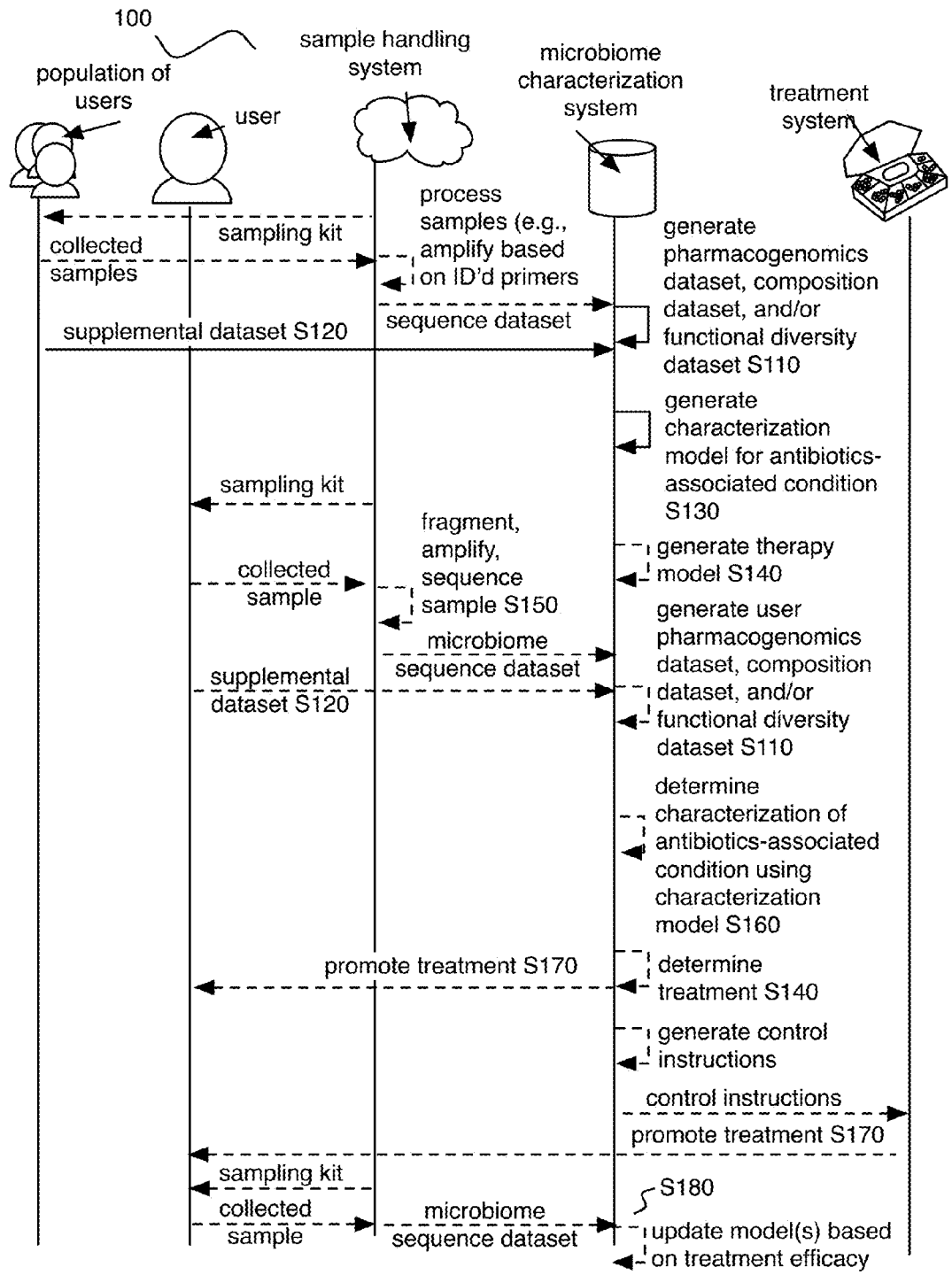

As shown in FIGS. 1A-1B, an embodiment of a method 100 for microbial pharmacogenomics for a user in relation to an antibiotics-associated condition can include: determining at least one of a microbiome pharmacogenomics dataset, a microbiome composition dataset, and a microbiome functional diversity dataset based on biological samples from a set of subjects S110; receiving a supplementary dataset, associated with at least a subset of the set of subjects, where the supplementary dataset is informative of the antibiotics-associated condition for the set of subjects S120; and performing a characterization process associated with the antibiotics-associated condition based on the supplementary dataset and features extracted from the at least one of the microbiome pharmacogenomics dataset, the microbiome composition dataset, and the microbiome functional diversity dataset S130. Embodiments of the method 100 can additionally or alternatively include determining a treatment (e.g., with an antibiotic therapy model) configured to modulate microorganism abundance, distributions, functional diversity and/or pharmacogenomics diversity in subjects characterized according to the characterization process S140; receiving a biological sample from a user S150; identifying a characterization of the user in relation to the antibiotics-associated condition based upon processing at least one of a microbiome pharmacogenomics dataset, a microbiome composition dataset, and a microbiome functional diversity dataset derived from the biological sample from the user, with the characterization process S160; promoting a treatment (e.g., antibiotic therapy, act.) to the subject based upon the characterization (e.g., and a therapy model, etc.) S170; and monitoring effectiveness of a therapy for the subject at different time points, based upon processing biological samples, to assess at least one of a microbiome pharmacogenomics profile, microbiome composition, and microbiome functional diversity S180. As such, the method 100 can be used for therapy monitoring, and can potentially be used for characterization as an intermediate step, in particular, for evaluation of one or more antibiotic therapies.

4.1 Method—Processing Datasets.

Block S110 recites: characterizing microbiome composition, function, and/or pharmacogenomics for each of an aggregate set of biological samples associated with a population of subjects, thereby generating at least one of a microbiome composition diversity dataset, a microbiome functional diversity dataset and a microbiome pharmacogenomics dataset for the population of subjects. Block S110 functions to process each of an aggregate set of biological samples, in order to determine compositional, functional and/or pharmacogenomics aspects associated with the microbiome of each of a population of subjects. Compositional, functional and pharmacogenomics aspects can include compositional aspects at the microorganism level, including parameters related to distribution of microorganisms across different groups of kingdoms, phyla, classes, orders, families, genera, species, subspecies, strains, and/or any other suitable infraspecies taxon (e.g., as measured in total abundance of each group, relative abundance of each group, total number of groups represented, etc.). Compositional, functional and pharmacogenomics aspects can also be represented in terms of operational taxonomic units (OTUs). Compositional, functional and pharmacogenomics aspects can additionally or alternatively include compositional aspects at the genetic level (e.g., regions determined by multilocus sequence typing, 16S rRNA sequences, 18S rRNA sequences, ITS sequences, protein-encoding sequences, other genetic markers, other phylogenetic markers, etc.). Compositional, functional, and pharmacogenomics aspects can include the presence or absence or the quantity of genes associated with specific functions (e.g., enzyme activities, transport functions, immune activities, antibiotic resistance genes, etc.). Outputs of Block S110 can thus be used to provide features of interest for the characterization process of Block S130, treatment process of Block S140, and/or other suitable portions of the method 100, where the features can be microorganism-based (e.g., presence of a genus of bacteria), genetic-based (e.g., based upon representation of specific genetic regions and/or sequences), functional-based (e.g., presence of a specific catalytic activity), pharmacogenomics-based (e.g. codon mutations, exon deletions or substitutions, gene rearrangements, translocations, etc.), and/or otherwise configured.

Additionally or alternatively, Block S130 (e.g., features associated with Block S130) can include but not limited to: nucleotide region or any other nucleotide-derived functional features (e.g., structural or regulatory RNAs, messenger RNAs, proteins or peptides) associated to resistance or metabolization of biologically active molecules. In particular, biologically active molecules can include, but not limited to: antibiotics, antibodies, peptides, hormones, and any other endogenous or exogenous molecules, regardless of its source (e.g., diet, environment). In a variation, the method 100 can include amplifying one or more full metagenomes (e.g., for complete microbial metagenome sequencing; as opposed to leveraging primers; in combination with primers; etc.) for any number of users (e.g., for an individual user, for an aggregate set of subjects such as a population of subjects). In a specific example, the method 100 can include: collecting biological samples from a set of users, including self-sampling from users; processing (e.g., isolating, amplifying, sequencing, aligning, etc.) the full metagenomes from the biological samples; determining at least one of a microbiome dataset, microbiome composition diversity features, microbiome functional diversity features, and microbiome pharmacogenomics features (e.g., prevalence of genes associated with antibiotic resistance or susceptibility, etc.); and determining a characterization (e.g., of an antibiotics-associated condition) and/or a therapy based on the features (and/or microbiome dataset). However, processing full metagenomes can be performed in any suitable manner.

In variations (e.g., in the context of clinical diagnosis and treatment), Block S110 can additionally or alternatively include analyzing and processing environmental samples (e.g., from a hospital environment of a subject, from a home environment of a subject, etc.), in order to inform the characterization and/or therapy models of subsequent blocks of the method 100. For instance, identification of microorganisms within an environment of a subject can be used to inform therapy models, in promoting therapies that prevent a subject from ever hosting a microorganism type present in the environment of the subject. However, environmental samples can be used in any other suitable manner to support the method 100.

In variations, sample processing in Block S110 can include any one or more of: lysing a biological sample, disrupting membranes in cells of a biological sample, separation of undesired elements (e.g., RNA, proteins) from the biological sample, purification of nucleic acids (e.g., DNA) in a biological sample, amplification (e.g., with a library preparation system) of nucleic acids from the biological sample, further purification of amplified nucleic acids of the biological sample, and sequencing of amplified nucleic acids of the biological sample.

In variations of Block S110, amplification of purified nucleic acids preferably includes at least one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique. In amplification of purified nucleic acids, the primers used are preferably selected to prevent or minimize amplification bias, as well as configured to amplify nucleic acid regions/sequences (e.g., of the 16S region, 18S region, ITS region, antibiotic resistant genes, etc.) that are informative taxonomically, phylogenetically, for diagnostics, for formulations (e.g., for probiotic formulations), for therapy, and/or for any other suitable purpose. Thus, universal primers (e.g., a F27-R338 primer set for 16S rRNA, a F515-R806 primer set for 16S rRNA, etc.) configured to avoid amplification bias can be used in amplification. Selected primers can additionally or alternatively be associated with (e.g., compatible with a genetic target, etc.) one or more antibiotics-associated conditions, microbiome pharmacogenomics features (e.g., primers compatible with microbiome mutations associated with antibiotic efficacy, such as point mutations in a gyrA gene and/or a parC gene, etc.), microbiome composition features (e.g., identified primers compatible with a genetic target corresponding to microbiome composition features associated with a group of taxa correlated with one or more sexually transmitted diseases, etc.), functional diversity features, supplementary features, and/or other features associated with antibiotic-associated conditions. For example, the primers can be complementary to genetic targets associated with the features (e.g., genetic sequences from which relative abundance features are derived; etc.). In a specific example, the method 100 can include: determining microorganism sequences based on: identifying a primer for a nucleic acid sequence associated with an antibiotics-associated condition, fragmenting nucleic acid material derived from biological samples associated with a set of users, and amplifying the fragmented nucleic acid material based on the primer (e.g., multiplex amplification using a bridge amplification substrate of a next generation sequencing platform, etc.); determining alignments of the microorganism sequences to a reference nucleic acid sequence set (e.g., including microbiome pharmacogenomics biomarkers associated with the antibiotic-associated conditions, etc.) associated with the antibiotics-associated condition; and determining microbiome pharmacogenomics data based on the alignments. Primers used in variations of Block S110 can additionally or alternatively include incorporated barcode sequences specific to each biological sample, which can facilitate identification of biological samples post-amplification. Primers used in variations of Block S110 can additionally or alternatively include adaptor regions configured to cooperate with sequencing techniques involving complementary adaptors (e.g., Illumina Sequencing). Additionally or alternatively, Block S110 can implement any other step configured to facilitate processing (e.g., using a Nextera kit).

In variations of Block S110, sequencing of purified nucleic acids can include methods involving targeted amplicon sequencing and/or metagenomic sequencing, implementing techniques including one or more of: sequencing-by-synthesis techniques (e.g., Illumina sequencing), capillary sequencing techniques (e.g., Sanger sequencing), pyrosequencing techniques, and nanopore sequencing techniques (e.g., using an Oxford Nanopore technique) or any other suitable sequencing technique.

In a specific example of Block S110, amplification and sequencing of nucleic acids from biological samples of the set of biological samples includes: solid-phase PCR involving bridge amplification of DNA fragments of the biological samples on a substrate with oligo adapters, where amplification involves primers having a forward index sequence (e.g., corresponding to an Illumina forward index for MiSeq/NextSeq/HiSeq platforms), a forward barcode sequence, a transposase sequence (e.g., corresponding to a transposase binding site for MiSeq/NextSeq/HiSeq platforms), a linker (e.g., a zero, one, or two-base fragment configured to reduce homogeneity and improve sequence results), an additional random base, a sequence for targeting a specific target region (e.g., 16S rRNA region, 18S rRNA region, ITS region, antibiotic resistant genes, etc.), a reverse index sequence (e.g., corresponding to an Illumina reverse index for MiSeq/NextSeq/HiSeq platforms), and a reverse barcode sequence. In the specific example, sequencing includes Illumina sequencing (e.g., with a HiSeq platform, with a MiSeq platform, with a NextSeq platform, etc.) using a sequencing-by-synthesis technique.

In variations, computational processing in Block S110 can include any one or more of: identification of microbiome-derived sequences (e.g., as opposed to subject sequences and contaminants), alignment and mapping of microbiome-derived sequences (e.g., alignment of fragmented sequences using one or more of single-ended alignment, ungapped alignment, gapped alignment, pairing, and/or other suitable techniques, such as for facilitating alignment to reference sequences associated with the antibiotics-associated condition, etc.), and generating features derived from compositional, functional and pharmacogenomics aspects of the microbiome associated with a biological sample.

Regarding Block S110, upon identification of represented groups of microorganisms of the microbiome associated with a biological sample, generating features derived from compositional, functional and pharmacogenomics aspects of the microbiome associated with a biological sample can be performed. In one variation, generating features can include generating features based upon multilocus sequence typing (MLST), in order to identify markers useful for characterization in subsequent blocks of the method 100. Additionally or alternatively, generated features can include generating features that describe the presence or absence of certain taxonomic groups of microorganisms, and/or ratios between exhibited taxonomic groups of microorganisms. Additionally or alternatively, generating features can include generating features describing at least one or more of: quantities of represented taxonomic groups, networks of represented taxonomic groups, functional groups and/or pharmacogenomics groups, correlations in representation of different taxonomic groups, functional groups and/or pharmacogenomics groups, interactions between different taxonomic groups, products produced by different taxonomic groups, interactions between products produced by different taxonomic groups, ratios between dead and alive microorganisms (e.g., for different represented taxonomic groups, based upon analysis of RNAs), phylogenetic distance (e.g., in terms of Kantorovich-Rubinstein distances, Wasserstein distances etc.), any other suitable taxonomic group-related feature(s), any other suitable genetic or functional feature(s), any other suitable pharmacogenomics feature(s).

Relating to Block S110, additionally or alternatively, generating features (e.g., for a microbiome dataset) can include generating features describing relative abundance of different microorganism groups, for instance, using a sparCC approach, using Genome Relative Abundance and Average size (GAAS) approach and/or using a Genome Relative Abundance using Mixture Model theory (GRAMMy) approach that uses sequence-similarity data to perform a maximum likelihood estimation of the relative abundance of one or more groups of microorganisms. Additionally or alternatively, generating features can include generating statistical measures of taxonomic variation, as derived from abundance metrics. Additionally or alternatively, generating features can include generating features derived from relative abundance factors (e.g., in relation to changes in abundance of a taxon, which affects abundance of other taxa). Additionally or alternatively, generating features can include generation of qualitative features describing presence of one or more taxonomic groups, in isolation and/or in combination. Additionally or alternatively, generating features can include generation of features related to genetic markers (e.g., representative 16S, 18S, and/or ITS sequences) characterizing microorganisms of the microbiome associated with a biological sample. Additionally or alternatively, generating features can include generation of features related to functional associations of specific genes and/or organisms having the specific genes. Additionally or alternatively, generating features can include generation of features related to pathogenicity of a taxon and/or products attributed to a taxon (e.g. genes for virulence factors, genomic island markers, etc.). Additionally or alternatively, generating features can include generation of features related to pharmacogenomics markers of a taxon or taxa of interest (e.g. detection of genes and/or mutations related to any kind of antibiotic resistance).

Block S110 and/or other suitable portions of the method 100 can, however, include generation of any other suitable feature(s) derived from sequencing and mapping of nucleic acids of a biological sample. For instance, the feature(s) can be combinatory (e.g., involving pairs, triplets), correlative (e.g., related to correlations between different features), and/or related to changes in features (e.g., temporal changes, changes across sample sites, spatial changes, etc.). However, Block S110 can be performed in any suitable manner.

Block S120 recites: receiving a supplementary dataset, associated with at least a subset of the set of subjects, where the supplementary dataset is informative of the antibiotics-associated condition for the set of subjects S120. Block S120 functions to acquire additional data associated with one or more subjects of the set of subjects, which can be used to train and/or validate the characterization process generated in Block S130. In Block S120, the supplementary dataset preferably includes survey-derived data, but can additionally or alternatively include any one or more of: contextual data derived from sensors and/or any other suitable components (e.g., components of the system 200, which can include treatment devices, user devices, etc.), medical data (e.g., current and historical medical data, such as antibiotics medical history), data informative of antibiotics-associated conditions (e.g., indications of presence or absence of the conditions, associated diagnoses, associated treatments, progress over time, etc.), and/or any other suitable type of data. In variations of Block S120 including reception of survey-derived data, the survey-derived data preferably provides physiological, demographic, and behavioral information in association with a subject. Additionally or alternatively Block S110 and Block S1120 can be performed in any manner analogous to U.S. application Ser. No. 15/097,862 filed 13 Apr. 2016, which is incorporated in its entirety by this reference. However processing supplementary datasets Block S120 can be performed in any suitable manner.

4.2 Performing a Characterization Process.

Figure 3:
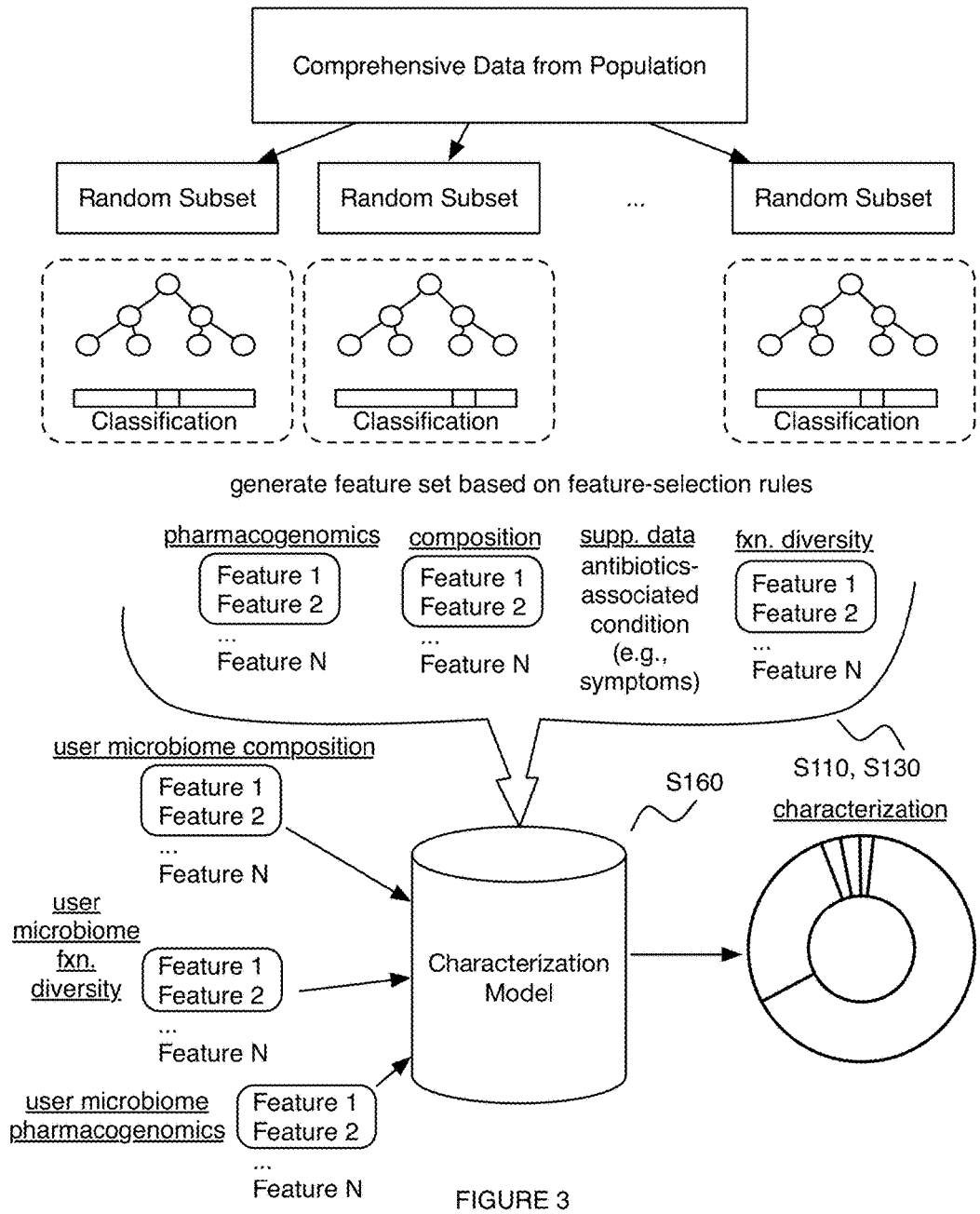
FIG. 3 depicts a variation of a process for generation of a model in an embodiment of a method and system for microbial pharmacogenomics.

Block S130 recites: performing a characterization process associated with the antibiotics-associated condition based on the supplementary dataset and features extracted from the at least one of the microbiome pharmacogenomics dataset, the microbiome composition dataset, and the microbiome functional diversity dataset S130. As shown in FIG. 3, Block S130 can function to identify features and/or feature combinations that can be used to characterize subjects or groups based upon their microbiome composition, functional features and/or pharmacogenomics features. As such, the characterization process can be used as a diagnostic tool that can characterize a subject (e.g., in terms of medical conditions, etc.) based upon their microbiome composition, functional features and/or pharmacogenomics features. Such characterization can then be used to suggest or provide personalized antibiotic therapies (and/or other therapies) by way of the therapy model of Block S140.

In performing the characterization process, Block S130 can use computational methods (e.g., statistical methods, machine learning methods, artificial intelligence methods, bioinformatics methods, etc.) to characterize a subject as exhibiting features characteristic of a group of subjects with a health condition that can be efficiently treated with a personalized therapy regimen (e.g., personalized antibiotic therapy regimen). In variations of Block S130, performing a characterization process can include generating one or more characterizations of one or more antibiotics-associated conditions. In examples, the characterization process of Block S130 can facilitate identification of correlations between antibiotics-associated conditions and upregulation or downregulation in relation to microbiome pharmacogenomics profiles (e.g., microbiome pharmacogenomics features correlated with antibiotics-associated conditions; etc.), microorganism population(s) (e.g., microbiome pharmacogenomics features, taxonomic groups, microbiome composition features, etc.), microbiome functional diversity (e.g., in relation to Clusters of Orthologous Groups/Kyoto Encyclopedia of Genes and Genomes pathways, microbiome functional diversity features, etc.) and/or other suitable aspects associated with the microbiome. Characterizing upregulation and/or downregulation can be at any suitable taxonomic level (e.g., kingdom, phylum, class, order, family, genus, species, strain, etc.), any suitable granularity of functional diversity, any suitable granularity of microbiome pharmacogenomics profile, and/or at any suitable granularity (e.g., chromosome, locus, gene, allele, locus, gene, nucleotide, etc.).

In another variation, characterizing a antibiotics-associated condition in Block S130 can include generating a diagnostic analysis (e.g., estimating a risk of being inflicted by the antibiotics-associated condition; calculating the change in risk conferred by an identified treatment; diagnosing the presence or absence of the antibiotics-associated condition, such as the presence or absence of microbiome pharmacogenomics features; diagnosing the severity of the antibiotics-associated condition over time in relation to microbiome pharmacogenomics, composition, and/or functional diversity; resistance and/or susceptibility to treatments such as antibiotics, etc.) and/or other analyses. In another variation of Block S130, characterizing an antibiotic-associated condition can be based on one or more supplementary datasets. For example, the set of feature-selection rules can correlate one or more antibiotics-associated conditions to one or more biometric features derived from biometric data informative of an antibiotics-associated condition (e.g., optical data associated with diagnosis of gonorrhea, another sexually transmitted disease, a urinary tract infection, and/or other suitable antibiotics-associated condition; data collected in association with supplementary medical devices, such as parameters for antibiotic delivery by antibiotic delivery devices; supplementary data associated with a sample collection site; blood data; temperature data; user behavior data; cardiovascular data; stool data; etc.). In another example, the supplementary dataset can include sensor data collected at a user device, supplementary medical device, and/or other suitable component (e.g., sample handling system, etc.). In another example, performing a characterization process can include determining a series of characterizations over time based on treatments promoted over time (e.g., therapy data including antibiotic regimen data, probiotic regimen data, and/or other suitable therapy data associated with a population of users), where the effect of different treatments over time can aid in illuminating insights associated with microbiome pharmacogenomics, microbiome compositions and/or functional diversity correlated with antibiotics-associated conditions. However, performing a characterization process based on supplementary datasets, and/or generating a diagnostic analysis, can be performed in any suitable manner.

Block S130 can additionally or alternatively generating features, which can function to generate one or more features for the characterization process (e.g., for use in generating a characterization model) and/or for other suitable processes of the method 100. Features can include any one or more of: microbiome pharmacogenomics features, microbiome composition features (e.g., absolute and/or relative abundance of taxonomic groups in a user's microbiome), microbiome functional diversity features, and/or other suitable features. Microbiome pharmacogenomics features can include features (e.g., in relation to an antibiotics-associated condition, related taxa, related functional diversity, etc.) associated with one or more: a codon mutation, an exon deletion, a substitution, a gene rearrangement, a translocation, microbial strain mutability, microbial strain resistance or susceptibility to antibiotics, microbial strain co-dependent behavior, microbial pharmacogenomics markers, and/or any other suitable features (e.g., relative abundance of such features, etc.). Microbiome functional diversity features can include any one or more of: Kyoto Encyclopedia of Genes and Genomes (KEGG) functional features (e.g., KEGG features associated with flagellum biosynthesis, etc.), Clusters of Orthologous Groups (COG) of proteins features, L2, L3, L4 derived features, genomic functional features, functional features associated with and/or specific to a taxonomic group, chemical functional features (e.g., cysteine metabolism, etc.), systemic functional features (e.g., systemic immune function; functions associated with systemic diseases; etc.), and/or any suitable functional features. Microbiome features can additionally or alternatively be derived from and/or associated with at least one of: relative abundance monotonic transformations, non-monotonic transformations, normalizations, feature vectors such as derived from at least one of linear latent variable analysis and non-linear latent variable analysis, linear regression, non-linear regression, kernel methods, feature embedding methods, machine learning, statistical inference methods and/or any other suitable approaches.

Regarding Block S130, determining features is preferably based on processing microbiome datasets according to one or more computer-implemented rules (e.g., a feature-selection rule, a user preference rule, etc.), but features can be determined based on any suitable information. For example, the method 100 can include obtaining a set of feature-selection rules (e.g., microbiome pharmacogenomics feature-selection rules, etc.) correlating the antibiotics-associated condition to a subset of microbiome pharmacogenomics features, microbiome composition features, and/or microbiome functional diversity features (e.g., from a pool of potential microbiome features); and generating features based on evaluating the microbiome datasets against the set of feature-selection rules, where the set of antibiotics-associated feature selection rules are operable to improve the microbiome characterization system (e.g., by facilitating decreased processing time such as for transforming supplementary data and features into a characterization model; by improving speed of model storage, retrieval, and/or execution; by improving characterization and/or treatment provision accuracy; etc.). In a specific example, feature-selection rules can be associated with a correlation between microbiome pharmacogenomics features and antibiotic efficacy in relation to one or more antibiotic-associated conditions (e.g., where the correlations can be determined based on processing a series of user biological samples over time to evaluate antibiotic efficacy in the context of the user's microbiome pharmacogenomics profile, microbiome composition, and/or microbiome functional diversity, etc.).

Block S130 and/or other portions of the method 100 preferably include applying computer-implemented rules to process population-level data, but can additionally or alternatively include applying computer-implemented rules to process microbiome-related data on a demographic-specific basis (e.g., subgroups sharing a demographic feature such as medical history associated with the antibiotic-associated condition and/or historic antibiotic treatments taken, ethnicity, age, gender, etc.), condition-specific basis (e.g., subgroups exhibiting a particular antibiotics-associated condition), a sample type-specific basis (e.g., applying different computer-implemented rules to process microbiome data derived from samples collected at different collection sites; applying different computer-implemented rules based on the type of supplementary data available to supplement the sample; etc.), and/or any other suitable basis. As such, Block S130 can include assigning users from the population of users to one or more subgroups; and applying different computer-implemented rules for determining features (e.g., the set of feature types used; the types of characterization models generated from the features; etc.) for the different subgroups. However, applying computer-implemented rules can be performed at any suitable level of granularity in any suitable manner.

Figure 12:
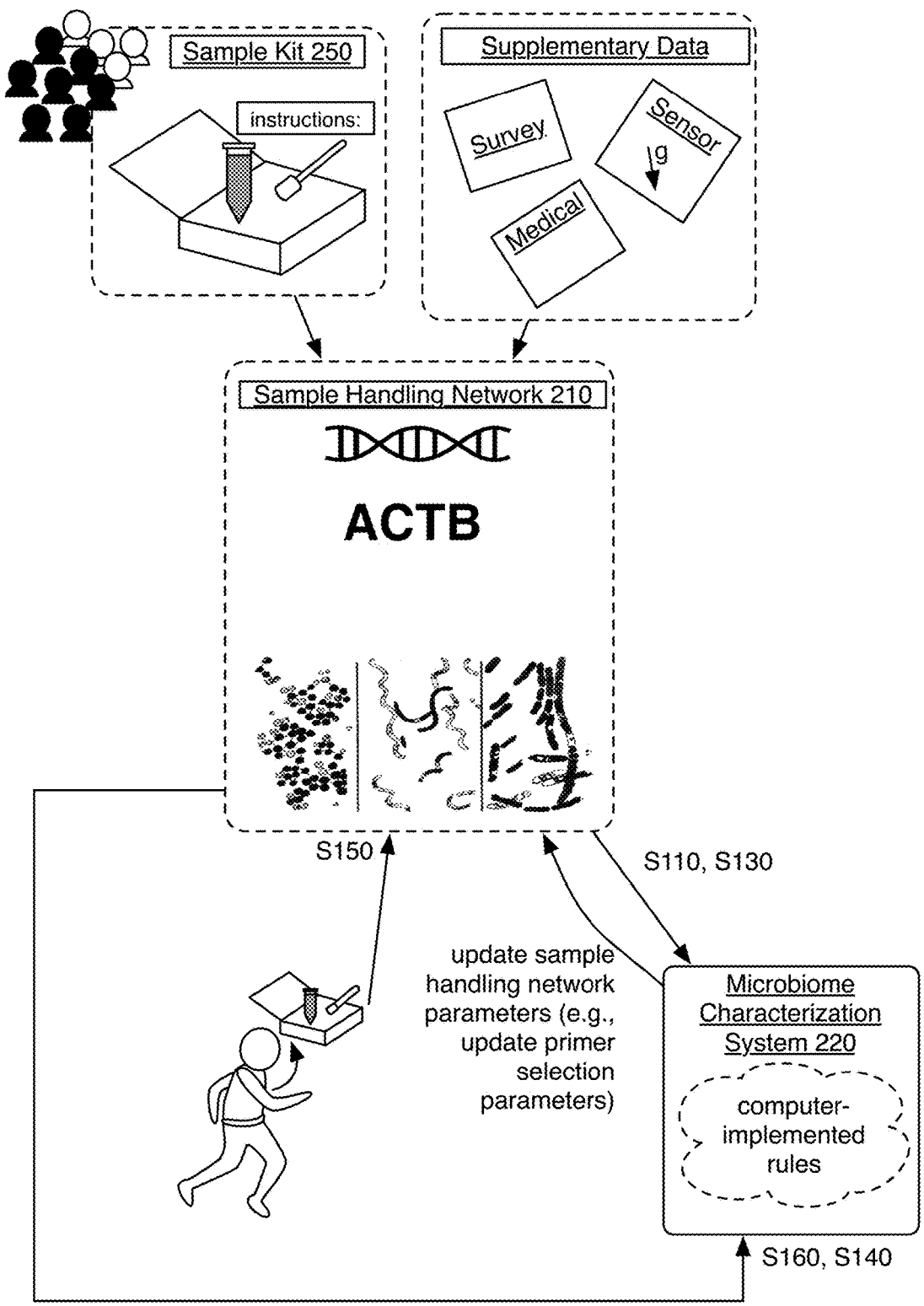
FIG. 12 depicts a variation of sample processing parameter modification in an embodiment of a method for microbial pharmacogenomics.

In a variation, Block S130 can include applying feature-selection rules (e.g., feature selection algorithms such as exhaustive, best first, simulated annealing, greedy forward, greedy backward, and/or other suitable feature selection algorithms) to filter, rank, and/or otherwise select features for use in generating one or more characterization models, therapy models (e.g., using rules correlating one or more treatments to different degrees of efficacy, to microbiome pharmacogenomics profiles, microbiome composition, microbiome functional diversity, and/or other suitable aspects, etc.), and/or other suitable models. In a variation, application of feature-selection rules can lead to microbiome-related insights upon which modifications in sample processing (e.g., techniques, experimental conditions, in Blocks S110-S120, S150, etc.) can be based. For example, the method 100 can include: applying a set of antibiotics-associated feature selection rules to identify features correlated (e.g., most correlated; etc.) with the antibiotics-associated conditions (e.g., presence, risk, therapies, etc.); and selecting primers (e.g., for use in amplification and sequencing to generate microbiome datasets; etc.) compatible with genetic targets associated with the identified features. As such, the feature-selection rules and/or other computer-implemented rules can additionally or alternatively function to determine sample processing parameters (e.g., described in relation to Blocks S110-S120, S150, etc.), as shown in FIG. 12. However, any suitable number and/or type of feature-selection rules can be applied in any manner to define one or more feature sets.

In an example, in Block S130, feature-selection rules can include application of a statistical analysis (e.g., an analysis of probability distributions) of similarities and/or differences between a first group of subjects exhibiting a target state (e.g., an antibiotic-associated condition state) and a second group of subjects not exhibiting the target state (e.g., a "normal" state). In implementing this variation, one or more of a Kolmogorov-Smirnov (KS) test, a permutation test, a Cramer-von Mises test, and any other statistical test (e.g., t-test, Welch's t-test, z-test, chi-squared test, test associated with distributions, etc.) can be used. In particular, one or more such statistical hypothesis tests can be used to assess a set of features having varying degrees of abundance in a first group of subjects exhibiting a target state (e.g., a sick state; a microbiome pharmacogenomics profile; etc.) and a second group of subjects not exhibiting the target state (e.g., having a normal state). In more detail, the set of features assessed can be constrained based upon percent abundance and/or any other suitable parameter pertaining to diversity in association with the first group of subjects and the second group of subjects, in order to increase or decrease confidence in the characterization. In a specific implementation of this example, a feature can be derived from a taxon of bacteria that is abundant in a certain percentage of subjects of the first group and subjects of the second group, where a relative abundance of the taxon between the first group of subjects and the second group of subjects can be determined from the KS test, with an indication of significance (e.g., in terms of p-value). Thus, an output of Block S130 can include a normalized relative abundance value (e.g., 25% greater abundance of a taxon in sick subjects vs. healthy subjects) with an indication of significance (e.g., a p-value of 0.0013). Variations of feature generation can additionally or alternatively implement or be derived from functional features, pharmacogenomics features or metadata features (e.g., non-bacterial markers). However, any suitable statistical analysis can be applied in any suitable manner.

In another variation, Block S130 can additionally or alternatively transform input data from at least one of the microbiome composition diversity dataset, microbiome functional diversity dataset, microbiome pharmacogenomics diversity dataset, a supplementary dataset, and/or other suitable datasets into feature vectors that can be tested for efficacy in predicting characterizations (e.g., diagnoses) of the population of subjects. Data from the supplementary dataset can additionally or alternatively be used to provide indication of one or more characterizations of a set of characterizations, where the characterization process is trained with a training dataset of candidate features and candidate classifications to identify features and/or feature combinations that have high degrees (or low degrees) of predictive power in accurately predicting a classification. As such, refinement of the characterization process with the training dataset identifies feature sets (e.g., of subject features, of combinations of features) having high correlation with specific classifications of subjects.

In variations of Block S130, feature vectors effective in predicting classifications of the characterization process can include features related to one or more of: microbiome diversity metrics (e.g., in relation to distribution across taxonomic groups, in relation to distribution across archaeal, bacterial, viral, and/or eukaryotic groups), presence of taxonomic groups in one's microbiome, representation of specific genetic sequences (e.g., 16S sequences) in one's microbiome, relative abundance of taxonomic groups in one's microbiome, microbiome resilience metrics (e.g., in response to a perturbation determined from the supplementary dataset), abundance of genes that encode proteins or RNAs with given functions (enzymes, transporters, proteins from the immune system, hormones, interference RNAs, etc.) and any other suitable features derived from the microbiome diversity dataset, the microbiome functional diversity dataset, the microbiome pharmacogenomics features dataset and/or the supplementary dataset. Additionally or alternatively, combinations of features can be used in a feature vector, where features can be grouped and/or weighted in providing a combined feature as part of a feature set. For example, one feature or feature set can include a weighted composite of the number of represented classes of bacteria in one's microbiome, presence of a specific genus of bacteria in one's microbiome, representation of a specific 16S sequence in one's microbiome, and relative abundance of a first phylum over a second phylum of bacteria. However, the feature vectors and features can additionally or alternatively be determined in any other suitable manner.

Block S130 can additionally or alternatively include generating a characterization model, which can function to generate one or more characterization models for one or more antibiotics-associated conditions based on applying one or more features, microbiome datasets, supplementary data, and/or any other suitable data. Characterization models (and/or therapy models or other suitable models) can include any one or more of: probabilistic properties, heuristic properties, deterministic properties, and/or any other suitable properties. Block S130 and/or other suitable portions of the method 100 (e.g., generating a therapy model S140) and/or system 200 can employ any one or more algorithms described in or analogous to U.S. application Ser. No. 15/097,862 filed 13 Apr. 2016, which is incorporated in its entirety by this reference, and/or can employ any suitable algorithm. In a variation of Block S130, the characterization process can be generated and trained according to a random forest predictor (RFP) algorithm that combines bagging (e.g., bootstrap aggregation) and selection of random sets of features from a training dataset to construct a set of decision trees, T, associated with the random sets of features. In using a random forest algorithm, N cases from the set of decision trees are sampled at random with replacement to create a subset of decision trees, and for each node, m prediction features are selected from all of the prediction features for assessment. The prediction feature that provides the best split at the node (e.g., according to an objective function) is used to perform the split (e.g., as a bifurcation at the node, as a trifurcation at the node). By sampling many times from a large dataset, the strength of the characterization process, in identifying features that are strong in predicting classifications can be increased substantially. In this variation, measures to prevent bias (e.g., sampling bias) and/or account for an amount of bias can be included during processing to increase robustness of the model. However, applying such models can be performed in any suitable manner.

Figure 6:
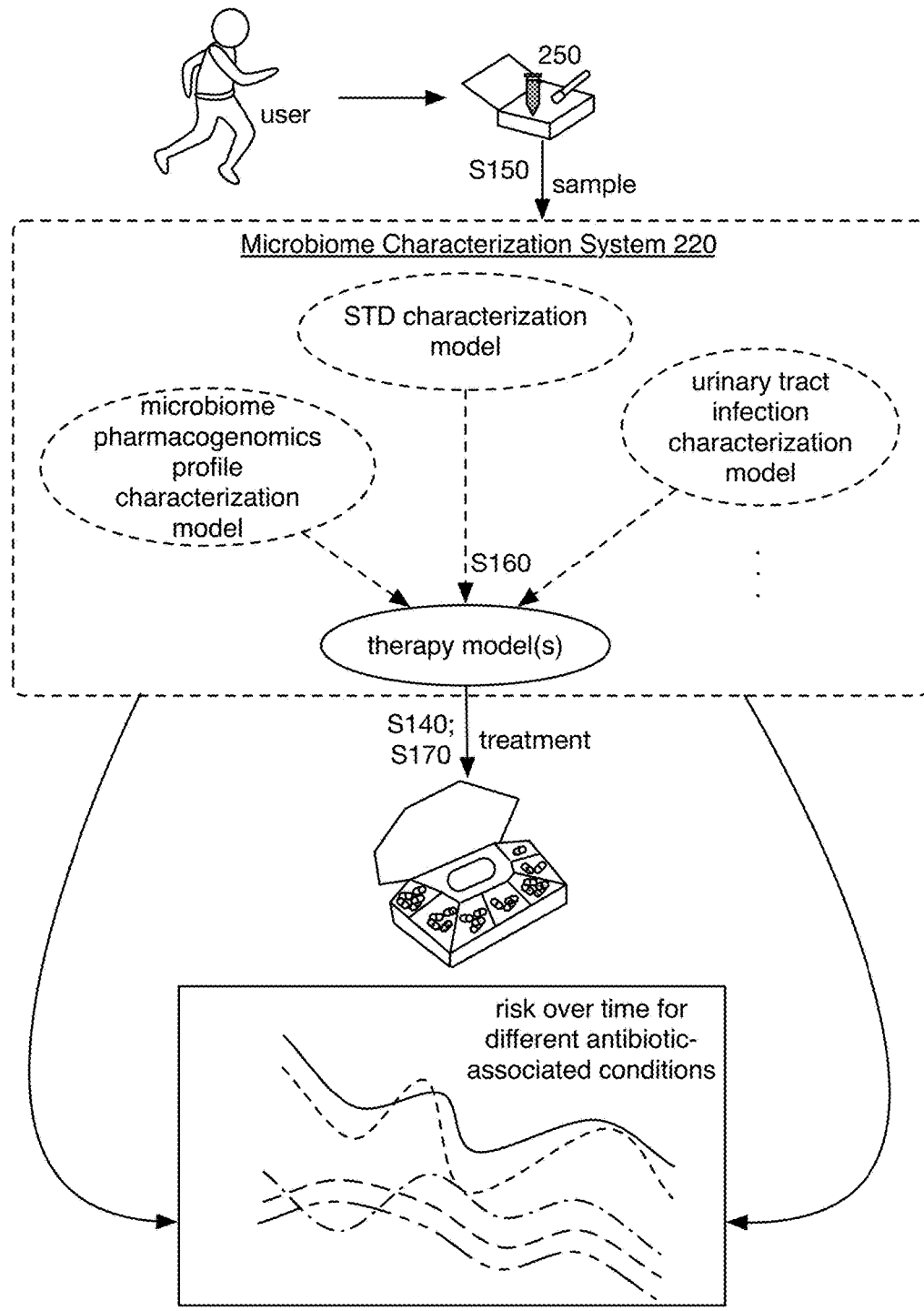
FIG. 6 depicts a variation of applying multiple models in an embodiment of a method for microbial pharmacogenomics.

In another variation of Block S130, different characterization models can be generated for different demographic groups (e.g., different characterization models for user subgroups associated with different antibiotic medical history; etc.), antibiotics-associated conditions (e.g., different characterization models for different antibiotics-treatable conditions; different characterization models for different microbiome pharmacogenomics profiles; etc.), individual subjects, supplementary data (e.g., models incorporating features derived from biometric sensor data and/or survey response data vs. models independent of supplementary data, etc.), and/or other suitable criteria. As shown in FIG. 6, characterizations outputted from different characterization models can be used in determining and/or promoting a therapy, such as by inputting outputs derived from different characterizations for different antibiotics-associated conditions (e.g., for different sexually transmitted diseases, urinary tract infections, etc.) into a therapy model (e.g., to generate a single therapy or a plurality of therapies tailored to treating the different antibiotics-associated conditions, etc.).

In another example, Block S130 can include selecting different characterization models for different user accounts; and for each user account, storing the corresponding characterization model in association with the user account in order to improve data storage and/or retrieval (e.g., for performing processes of the method 100, etc.). Generating a plurality of characterization models suited to different contexts can confer improvements to the microbiome characterization system by improving characterization accuracy (e.g., by tailoring analysis to a particular subject's demographic, antibiotic-associated condition, features, etc.), retrieval speed for the appropriate characterization model from a database (e.g., by associating customized characterization models with particular user accounts and/or other identifiers), generation and/or execution of characterization models (e.g., where the customized models are associated with a subset of a pool of potential features correlated with antibiotics-associated conditions, and where the remaining unselected features are less correlated with the antibiotics-associated conditions), and/or other suitable aspects of the microbiome characterization system.

In another variation of Block S130, generating feature sets for different characterization models (and/or other models) can be based on different feature selection rules (e.g., applying different sets of microbiome pharmacogenomics feature-selection rules to generate different feature sets specific to different sexually transmitted diseases; etc.). Alternatively, overlapping or the same set of feature selection rules can be used for generating different characterization models (e.g., using the same microbiome pharmacogenomics feature in generating two different characterization models, etc.). Additionally or alternatively, generating any number of characterization models can be performed in any suitable manner. However, performing a characterization process S130 can be performed in any suitable manner.

4.2.A Method—Antibiotics-Associated Condition Characterization

In one implementation, a characterization process of Block S130 based upon statistical analyses can identify the sets of features that have the highest correlations with an antibiotics-treatable disease (e.g., a sexually transmitted disease, STD) in a manner that is culture-free and/or implements self-sampling by the patient, thereby significantly decreasing the time-lag for an individual to receive treatment. In a specific example of this implementation, a characterization process of Block S130 can be used as a diagnostic test to identify and characterize the strain(s) of gonorrhea present in samples, based on multiplexed PCR of genetic material of the samples, and in terms of one or more of: mutability (e.g., mutation type, mutation tendency, rate of mutation, etc.) of a strain, resistance to types of antibiotics by a strain, co-dependent behavior (e.g., in terms of interferences in functional behavior, in terms of upregulation, in terms of downregulation, etc.) of a strain relative to presence or absence of other microorganisms present in a subject, and any other suitable aspect of interest in informing models for personalized therapy provision. As such, the characterization processes of Block S130 can include characterizing strains of an STD-associated microorganism (e.g., gonorrhea) present in a sample upon identifying microbial genetic features.

In variations of Block S130, microbiome features can be associated with *Neisseria gonorrhoeae* (species). In a specific example, the microbiome features can include point mutation features associated with point mutations in at least one of a gyrA gene and a parC gene for a taxon (e.g., *N. gonorrhoeae*), which can be associated with ciprofloxacin resistance. In another specific example, the microbiome features can be associated with presence of a mosaic penA allele, which can be associated with cephalosporin resistance. Such correlations and/or other suitable correlations between microbiome features and treatment efficacy can be used in determining and/or promoting treatments. However, any microbiome features can include any suitable microbiome pharmacogenomics features associated with any suitable taxon and/or any suitable resistance or susceptibility to antibiotics. Characterization in relation to gonorrhea and/or other suitable antibiotic-associated conditions can additionally or alternatively be performed in an analogous manner to processes described in U.S. application Ser. No. 15/097,862 filed 13 Apr. 2016, which is incorporated in its entirety by this reference.

4.3 Method—Personalization.

Figure 8:
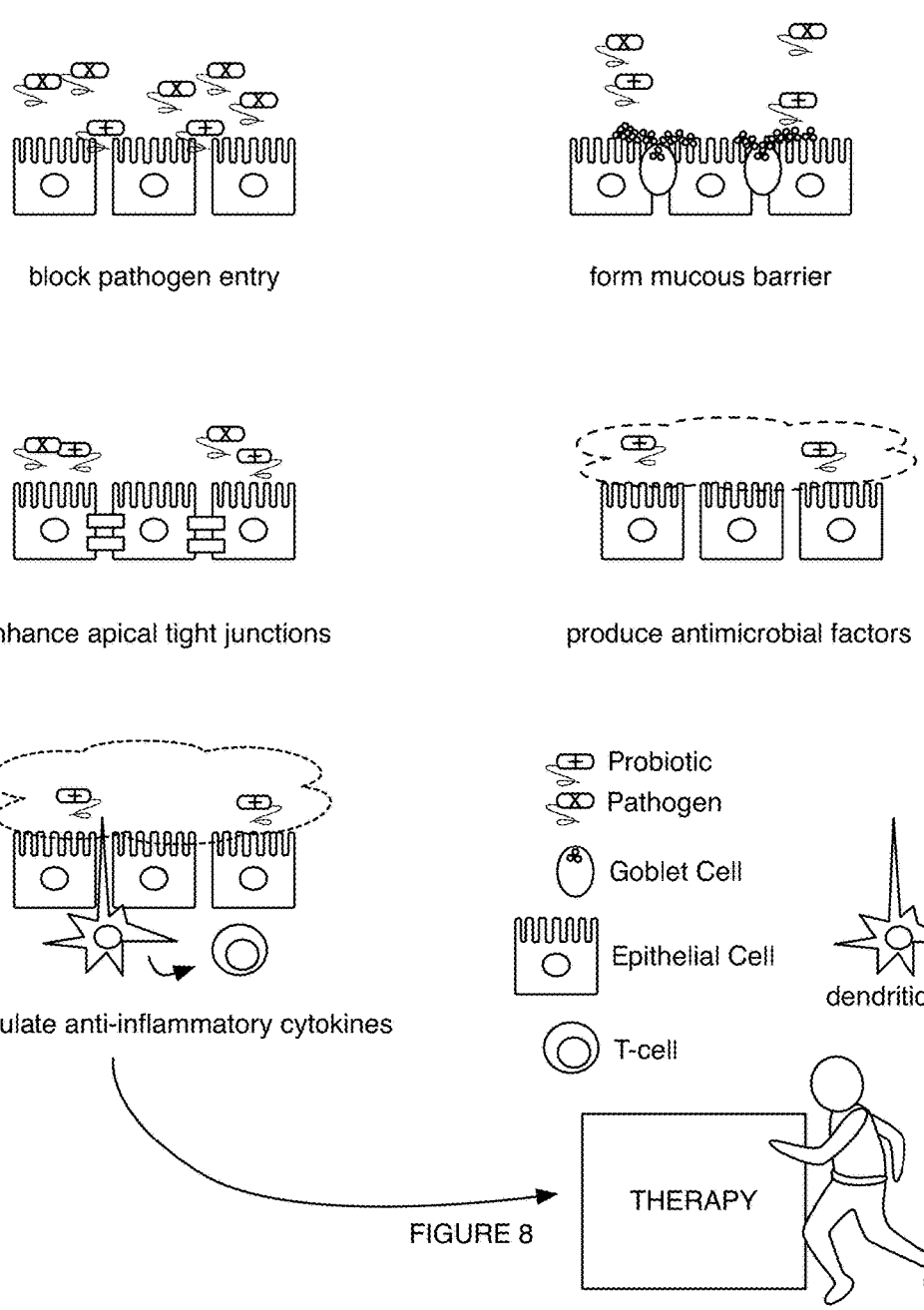
FIG. 8 depicts variations of mechanisms by which probiotic-based therapies operate in an embodiment of a method for microbial pharmacogenomics.

The method 100 can additionally or alternatively include Block S140, which recites: determining a treatment configured to modulate microorganism abundance, distributions, functional diversity and/or pharmacogenomics diversity in subjects characterized according to the characterization process S140. Block S140 functions to identify and/or predict therapies (e.g., antibiotic therapy regimens, etc.) that can correct or otherwise treat an antibiotics-treatable condition that the subjects have. Block S140 can additionally or alternatively include generating and/or applying a therapy model for determining the therapy. In Block S140, the treatments can additionally or alternatively be selected from therapies including one or more of: antibiotic-based therapies, probiotic-based therapies (e.g., as shown in FIG. 8), antifungal therapies, phage-based therapies, prebiotic-based therapies, small molecule-based therapies, medication-based therapies, diet-related therapies, topical therapies, cognitive/behavioral therapies, physical therapies, clinical therapies, alternative medicine-based therapies, environmental-based therapies (e.g., light-based therapies, temperature-based therapies, etc.) and/or any other suitable therapy designed to operate in any other suitable manner (e.g., in promoting a user's health in relation to an antibiotics-associated condition; etc.). Antibiotic-based therapies can include any one or more of: cell wall-based antibiotics (e.g., penicillins, cephalosporins, etc.), bacterial enzyme-based antibiotics (e.g., rifamycins, lipiarmycins, quinolones, sulfonamides, etc.), cell membrane-based antibiotics (e.g., polymyxins, etc.), bactericidal-based antibiotics, protein-synthesis-based antibiotics (e.g., macrolides, lincosamides, tetracyclines, etc.), cyclic lipopeptides, glycylcyclines, oxazolidinones, therapies associated with supplementary medical devices and/or other treatment systems, and/or any other suitable antibiotic-based therapies.

Figure 4:
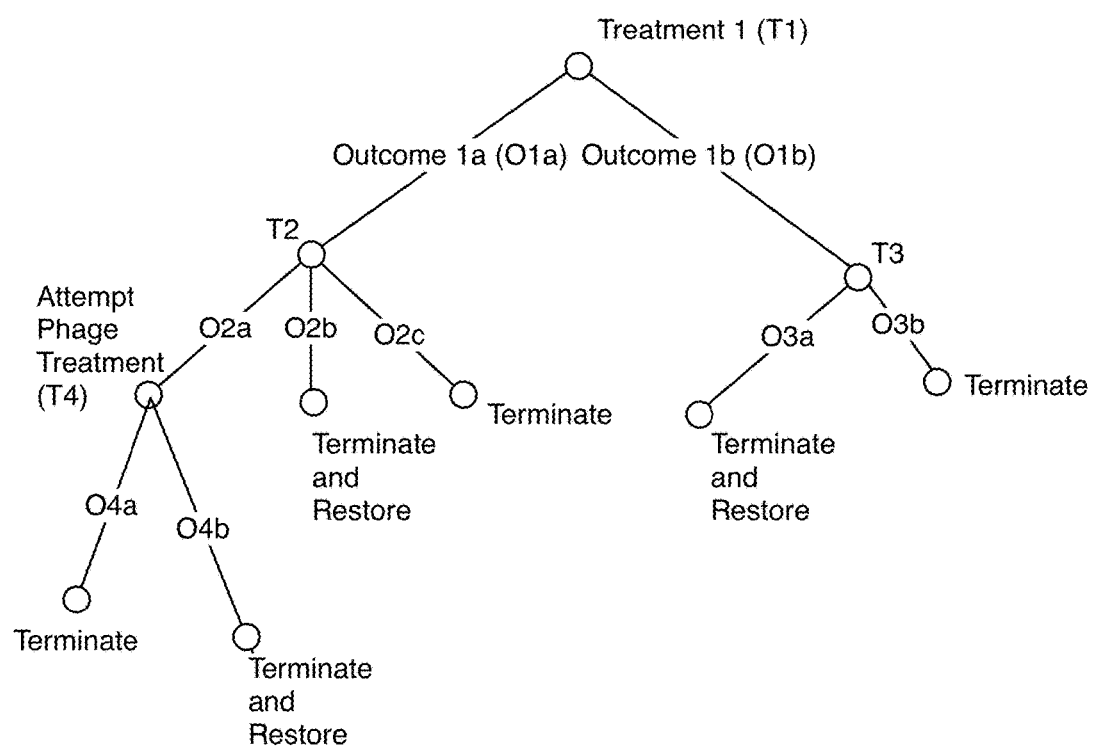
FIG. 4 depicts a variation of an output of a therapy model in an embodiment of a method and system for microbial pharmacogenomics.

In variations of Block S140, the therapy model can include an antibiotic therapy model including a decision tree/decision graph that arranges available antibiotics (e.g., specific antibiotic types, antibiotic doses, etc.) at nodes of the tree/graph in manner that prioritizes the most appropriate antibiotics and their doses to provide at each stage of a treatment plan, as shown in FIG. 4. Arrangement of stages of treatment can be based upon weighing of the positive consequences (e.g., minimized effect on beneficial bacterial populations of a subject) and/or negative consequences (e.g., risk of pernicious infection) of applying a specific antibiotic treatment to a subject, whereby the most effective, but least harmful antibiotics that target a disease-associated strain are promoted earlier in the treatment plan. In traversing branches of the decision tree/graph, patient indications and/or outcomes after application of the antibiotic at the upstream node can be used to promote application of antibiotics at downstream nodes. Alternatively, once the patient is treated, further promotion of antibiotic treatment can terminate, and restorative treatments (e.g., probiotic supplements generated by variations of the therapy model) can be promoted to a subject. However, the antibiotic therapy model can include any suitable properties and/or apply any suitable algorithm in determining any suitable aspects associated with antibiotic treatment.

Regarding Block S140, additionally or alternatively, outputs of the antibiotic therapy model can include a predictive model that describes predicted outcomes and/or consequences of application of different antibiotic treatments/doses to a subject, and allows another entity to make a decision in providing one or more antibiotics to the subject. Relating to Block S140, as such, an antibiotic therapy can be tailored to a subject based on one or more of: their condition (e.g., strain(s) of microorganisms present associated with a disease; microorganism genetic sequences associated with resistance and/or susceptibility to antibiotics.); abundance/spread of strains associated with their condition; demographic and/or behavioral characteristics of the subject; other microorganism populations of the subject; considerations derived from the environment of the subject; and any other suitable factors. In a specific example of a phage-based therapy, one or more populations (e.g., in terms of colony forming units) of phages specific to a certain bacteria (or other microorganism) represented in the subject can be used to down-regulate or otherwise eliminate populations of the certain bacteria associated with a disease or condition of a subject. As such, phage-based therapies can be used to reduce the size(s) of the undesired population(s) of bacteria (or other microorganisms) represented in the subject. Complementarily, phage-based therapies can be used to increase the relative abundances of bacterial populations not targeted by the phage(s) used.

Figure 7:
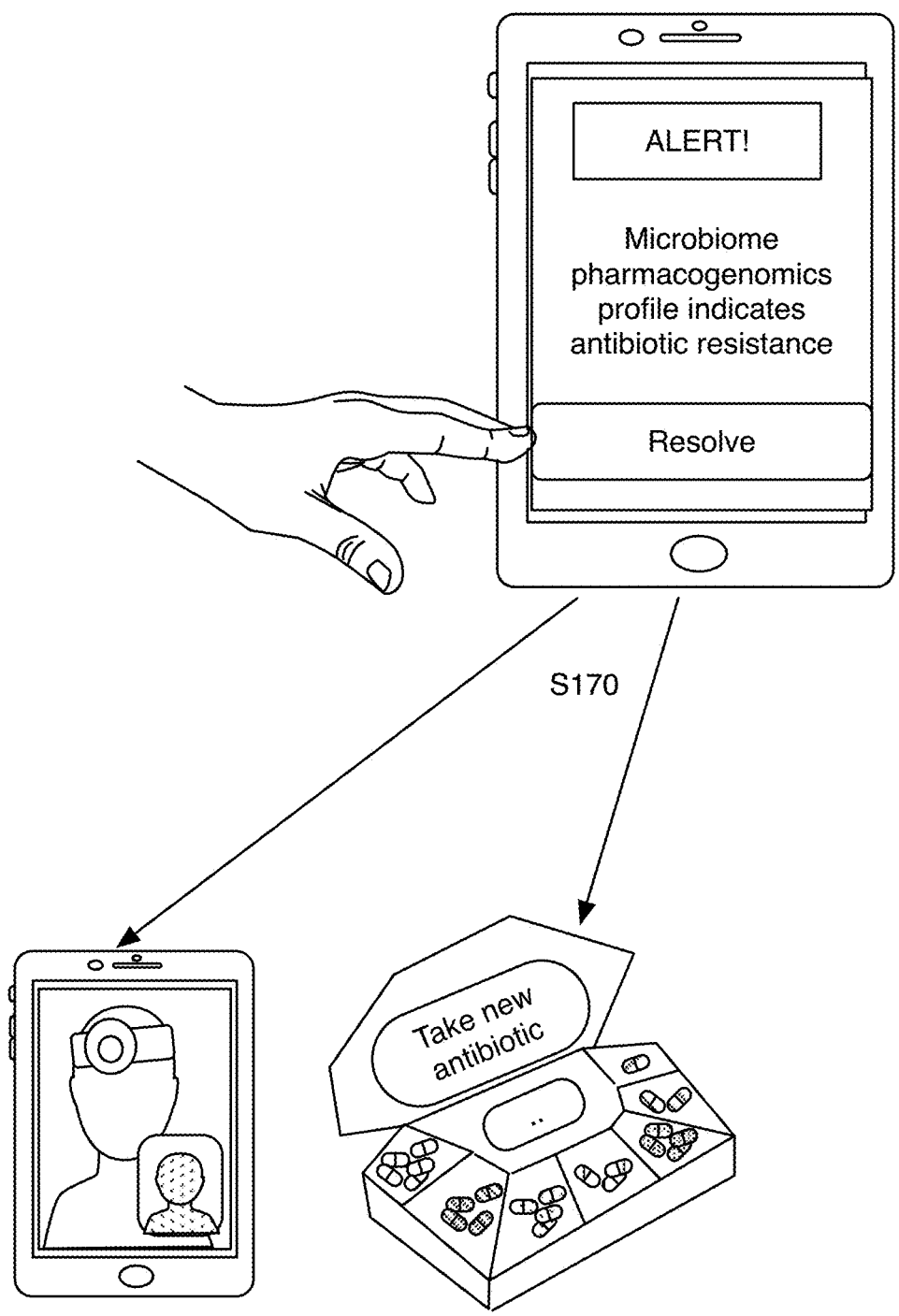
FIG. 7 depicts a variation of promoting therapies in variations of an embodiment of a method for microbial pharmacogenomics.

In a variation, Blocks S140 and/or S170 can include automatically initiating a signal that controls a treatment system to promote the therapy (e.g., based on a characterization, a therapy model output, etc.), where initiating the signal can include one or more of: generating and transmitting control instructions to a treatment system (e.g., controlling a antibiotic delivery device to provide an antibiotic to a user, etc.), initiating notification provision (e.g., to inform a user regarding one or more characterizations and/or treatments, etc.), and/or any other suitable operation in controlling treatment systems to promote therapies. In another variation, Block S140 can include facilitating an interaction between a user and a care provider (e.g., scheduling an appointment with a care provider; initiating a telemedicine conference over a wireless communication channel, as shown in FIG. 7; etc.), such as in response to and/or concurrently with a trigger event (e.g., characterizing an antibiotics-associated condition risk exceeding a threshold; manual request by a user and/or care provider; identifying a treatment efficacy below a threshold based on analysis of post-therapy biological samples; etc.). However facilitating interactions between users can be performed in any suitable manner.

In a variation of Block S140, generating and/or applying a therapy model can be based on one or more causes for an antibiotics-associated condition (e.g., a cause of an antibiotics-associated condition risk), where the therapy determined by the therapy model can be operable to reduce the antibiotics-associated condition risk. Regarding Block S140, processing of therapy models can be analogous to processing of characterization models (e.g., described for Block S130), where any number and/or types of therapy models can be generated for different purposes. In relation to Block S140, the therapy model can be derived in relation to identification of a "normal" or baseline microbiome composition, functional features, and/or pharmacogenomics features as assessed from subjects of a population of subjects who are identified to be in good health. Upon identification of a subset of subjects of the population of subjects who are characterized to be in good health (e.g., using features of the characterization process), therapies that modulate microbiome compositions, functional features and/or pharmacogenomics features toward those of subjects in good health can be generated in Block S140. Block S140 can thus include identification of one or more baseline microbiome compositions, functional features and/or pharmacogenomics features (e.g., one baseline microbiome for each of a set of demographics), and potential therapy formulations and therapy regimens that can shift microbiomes of subjects who are in a state of dysbiosis toward one of the identified baseline microbiome compositions, functional compositions and/or pharmacogenomics compositions. The therapy model can, however, be generated and/or refined in any other suitable manner.

In a variation, Blocks S140 and/or S170 can include deriving a therapeutic composition (e.g., an antibiotic treatment) associated with at least one of microbiome pharmacogenomics (e.g., deriving an antibiotic treatment designed to circumvent an antibiotic resistance or to attack an antibiotic susceptibility identified by a microbiome pharmacogenomics profile; etc.), microbiome composition and/or functional diversity (e.g., extracted features). In an example, the method 100 can include determining a modulator of a biomolecule associated with the antibiotics-associated condition (e.g., a modulator of a biomolecule derived from a set of taxa associated with the antibiotics-associated condition); deriving a therapeutic composition for the antibiotics-associated condition based on the modulator; and promoting the therapeutic composition. However determining and/or promoting treatments can be performed in any manner analogous to U.S. application Ser. No. 15/097,862 filed 13 Apr. 2016, which is incorporated in its entirety by this reference, and/or can be performed in any suitable manner.

The method 100 can additionally or alternatively include Block S150, which recites: receiving a biological sample from a user. Block S150 can function to facilitate generation of a microbiome dataset for the subject that can be used to derive inputs for the characterization process. As such, receiving, processing, and analyzing the biological sample preferably facilitates generation of a microbiome dataset for the subject, which can be used to provide inputs for a characterization process. Processing and analyzing the biological sample from the subject is preferably performed in a manner similar to that of one of the embodiments, variations, and/or examples of sample reception described in relation to Block S110 above. Additionally or alternatively, processing a biological sample can be performed in any manner analogous to U.S. application Ser. No. 15/097,862 filed 13 Apr. 2016, which is incorporated in its entirety by this reference. However, biological sample reception and processing in Block S150 can alternatively be performed in any other suitable manner.

The method 100 can additionally or alternatively include Block S160, which recites: identifying a characterization of the user in relation to the antibiotics-associated condition based upon processing at least one of a microbiome pharmacogenomics dataset, a microbiome composition dataset, and a microbiome functional diversity dataset derived from the biological sample from the user, with the characterization process. Block S160 can function to extract features from microbiome-derived data of the subject (e.g., based on evaluating the microbiome datasets against computer-implemented rules), and use the features as inputs into an embodiment, variation, or example of the characterization process described in Block S130 above and/or into any suitable process of the method 100. Identifying the characterization in Block S160 thus preferably includes identifying features and/or combinations of features associated with the microbiome composition, functional composition and/or pharmacogenomics composition of the subject's microbiome sample, inputting the features into the characterization process, and receiving an output that characterizes the subject as belonging to one or more of: a behavioral group, a gender group, a dietary group, a disease-state group, and any other suitable group capable of being identified by the characterization process. Block S160 can further include generation of and/or output of a confidence metric associated with the characterization of the subject. For instance, a confidence metric can be derived from the number of features used to generate the characterization, relative weights or rankings of features used to generate the characterization, measures of bias in the characterization process, and/or any other suitable parameter associated with aspects of the characterization process. In some variations, features extracted from the microbiome dataset of the subject can be supplemented with survey-derived and/or medical history-derived features from the subject, which can be used to further refine the characterization process of Block S130. However, the microbiome dataset of the subject can additionally or alternatively be used in any other suitable manner to enhance the models of the method 100, and Bock S160 can be performed in any suitable manner.

4.4 Method—Promoting and Monitoring a Therapy.

Figure 5:
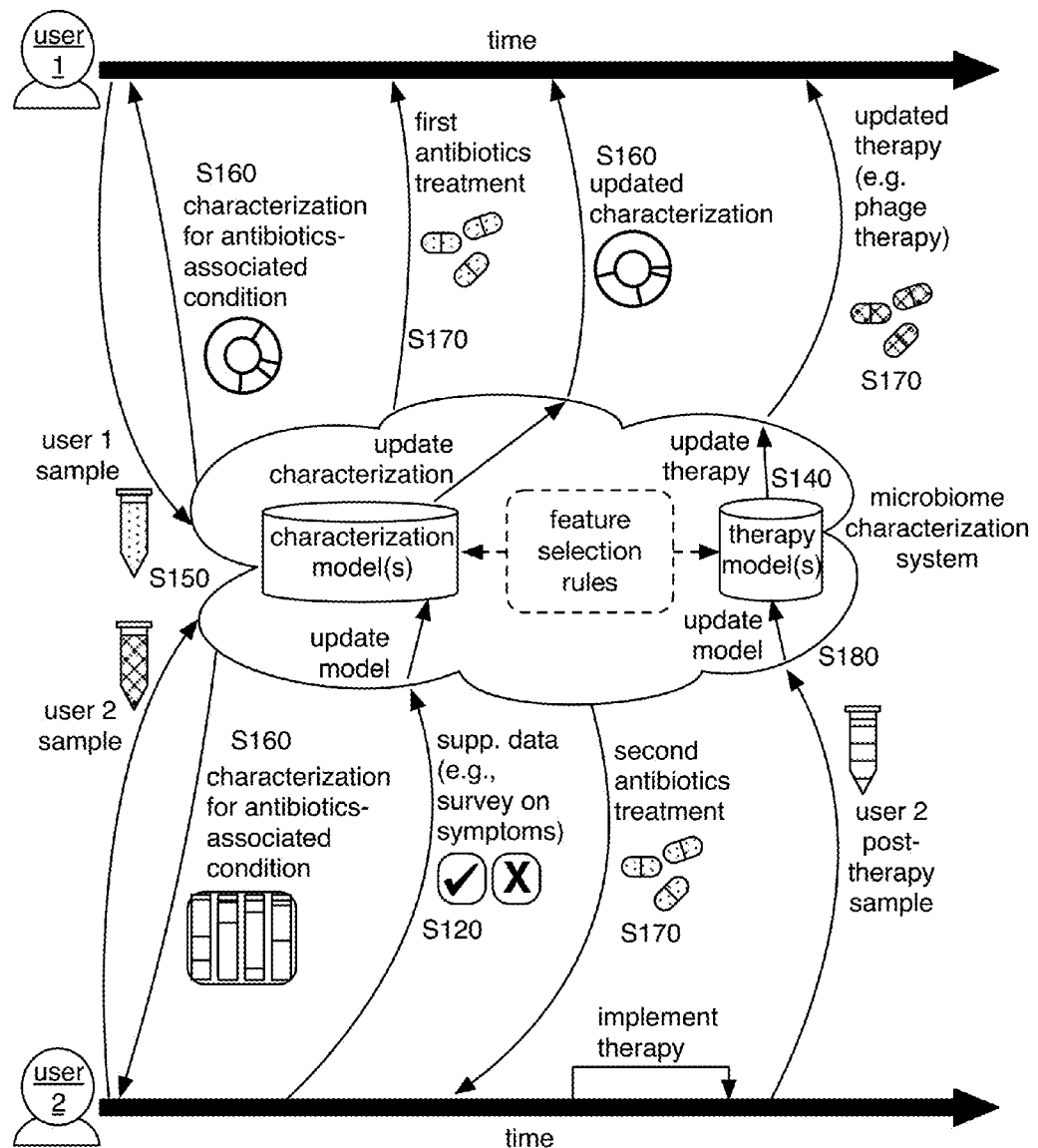
FIG. 5 depicts a variation of applying models in an embodiment of a method for microbial pharmacogenomics.

The method 100 can additionally or alternatively include Block S170, which recites: promoting a treatment (e.g., antibiotic therapy, act.) to the subject based upon the characterization (e.g., and a therapy model, etc.). Block S170 can function to recommend and/or provide a personalized therapy to the subject, in order to shift the microbiome composition, functional features and/or pharmacogenomics features of the subject toward a desired equilibrium state. Block S170 can include provision of a customized therapy to the subject according to their microbiome composition, functional features and pharmacogenomics features, as shown in FIG. 5, where the customized therapy is a formulation of antibiotics configured to correct a condition of subjects having the identified characterization. As such, outputs of Block S140 can be used to directly promote a customized therapy formulation and regimen (e.g., dosage, usage instructions) to the subject based upon a trained therapy model. Additionally or alternatively, therapy provision can include recommendation of available therapeutic measures configured to shift microbiome composition, functional features and/or pharmacogenomics features toward a desired state.

Antibiotic therapy provision in Block S170 can include provision of notifications to a subject regarding the recommended therapy and/or other forms of therapy. In one example, a web interface of a personal computer or laptop associated with a subject can provide access, by the subject, to a user account of the subject, where the user account includes information regarding the user's characterization, detailed characterization of aspects of the user's microbiome, and notifications regarding suggested therapeutic measures generated in Blocks S140 and/or S170. In another example, an application executing at a personal electronic device (e.g., smart phone, smart watch, head-mounted smart device) can be configured to provide notifications (e.g., at a display, haptically, in an auditory manner, etc.) regarding therapy suggestions generated by the therapy model of Block S170. Notifications and/or probiotic therapies can additionally or alternatively be provided directly through an entity associated with a subject (e.g., a caretaker, a spouse, a significant other, a healthcare professional, etc.). In some further variations, notifications can additionally or alternatively be provided to an entity (e.g., healthcare professional) associated with a subject, where the entity is able to administer the therapy measure (e.g., by way of prescription, by way of conducting a therapeutic session, etc.). Notifications can, however, be provided for therapy administration to a subject in any other suitable manner.

The method 100 can additionally or alternatively include Block S180, which recites: monitoring effectiveness of a therapy for the subject at different time points, based upon processing biological samples, to assess at least one of a microbiome pharmacogenomics profile, microbiome composition, and microbiome functional diversity. Block S180 can function to gather additional data regarding positive effects, negative effects, and/or lack of effectiveness of a probiotic therapy suggested by the therapy model for subjects of a given characterization, where the additional data can be used, for example, to generate, update, and/or execute one or more characterization models, therapy models, and/or other suitable models, and/or can be used in any suitable portion of the method 100. For example, the method 100 can include updating a model (e.g., characterization model, therapy model, etc.) based on one or more microbiome datasets (e.g., updated microbiome features extracted from updated microbiome datasets derived from post-therapy biological samples from a user; etc.), such as updating the model based on an observed modulation of a microbiome pharmacogenomics profile, microbiome composition, microbiome functional diversity, and/or other suitable microbiome aspect (e.g., in relation to an antibiotics-associated condition; such as determined based on comparisons of pre-therapy and post-therapy microbiome datasets. In another example, the method 100 can include, in response to updating a model, determining an update (e.g., to a characterization, to a therapy, etc.) for a user (e.g., a second user associated with a biological sample that the update was not based upon, etc.) in relation to the antibiotics-associated condition, based on the updated model. In another example, the method 100 can include: receiving a post-therapy biological sample from the user (e.g., after promoting the therapy); generating a post-therapy characterization of the user in relation to the antibiotics-associated condition based on the post-therapy biological sample (e.g., based on updated microbiome features derived from the post-therapy biological sample, where the microbiome features can be used with a characterization model, etc.); characterizing modulation of the antibiotic-associated condition based on the post-therapy characterization (e.g., and one or more pre-therapy characterizations for the user, for a second user, etc.); and/or promoting an updated therapy to the user based on the updated characterization. However, any suitable portion of the method 100 and/or any suitable operation can be performed in any suitable manner (e.g., for any number of users) based on post-therapy biological samples and/or updated microbiome datasets. Monitoring of a subject during the course of a therapy promoted by the therapy model (e.g., by receiving and analyzing biological samples from the subject throughout therapy, by receiving survey-derived data from the subject throughout therapy) can thus be used to generate a therapy-effectiveness model for each characterization provided by the characterization process of Block S130, and each recommended therapy measure provided in Blocks S140 and S170.

In Block S180, the subject can be prompted to provide additional biological samples at one or more key time points of a therapy regimen that incorporates the therapy, and the additional biological sample(s) can be processed and analyzed (e.g., in a manner similar to that described in relation to Block S120) to generate metrics characterizing modulation of the subject's microbiome composition, functional features and/or pharmacogenomics features. For instance, metrics related to one or more of: a change in relative abundance of one or more taxonomic groups represented in the subject's microbiome at an earlier time point, a change in representation of a specific taxonomic group of the subject's microbiome, a ratio between abundance of a first taxonomic group of bacteria and abundance of a second taxonomic group of bacteria of the subject's microbiome, a change in relative abundance of one or more functional families in a subject's microbiome, and any other suitable metrics can be used to assess therapy effectiveness from changes in microbiome composition, functional features and/or pharmacogenomics features. Additionally or alternatively, survey-derived data from the subject, pertaining to experiences of the subject while on the therapy (e.g., experienced side effects, personal assessment of improvement, etc.) can be used to determine effectiveness of the therapy in Block S180. However, monitoring effectiveness of one or more treatments, and/or performing processes based on the effectiveness can be performed in any suitable manner.

The method 100 and/or system of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which includes one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions. The embodiments include every combination and permutation of the various system components and the various method processes, including any variations, examples, and specific examples. As a person skilled in the art will recognize from the previous detailed description and from the figures and claims, modifications and changes can be made to the embodiments of the invention without departing from the scope of this invention as defined in the following claims.

We claim:

1. A system for evaluating an antibiotics-treatable condition in relation to a user, the system comprising:
 a handling system operable to collect containers comprising material from a set of users, the handling system comprising a sequencer system operable to determine microorganism sequences from the material;
 a microbiome characterization system operable to:
  determine microbiome pharmacogenomics data and at least one of microbiome composition data and microbiome functional diversity data based on the microorganism sequences,
  collect supplementary data associated with the antibiotics-treatable condition for the set of users, and
  transform the supplementary data and features extracted from the microbiome pharmacogenomics data and the at least one of microbiome composition data and the microbiome functional diversity data into a characterization model associated with the antibiotics-treatable condition; and
 a treatment system operable to:
  provide a treatment to the user for the antibiotics-treatable condition based on characterizing user material with the characterization model in relation to the antibiotics-treatable condition.

2. The system of claim 1, wherein the handling system is operable to determine the microorganism sequences based on amplifying nucleic acid material from the material using a primer for a nucleic acid sequence associated with the antibiotics-treatable condition.

3. The system of claim 1, wherein the handling system is operable to collect a user container comprising the user material, wherein the treatment system is operable to provide the treatment based on characterizing the user material, and wherein the treatment is operable to modulate a user microbiome composition for improving a state of the antibiotics-treatable condition.

4. The system of claim 1, wherein the features comprise microbiome pharmacogenomics features associated with at least one of a codon mutation, an exon deletion, a substitution, a gene rearrangement, and a translocation for a taxon associated with the antibiotics-treatable condition.

5. The system of claim 4, wherein the microbiome pharmacogenomics features are associated with at least one of microbial strain mutability, microbial strain resistance to antibiotics, and microbial strain co-dependent behavior.

6. The system of claim 4, wherein the microbiome pharmacogenomics features are associated with a relative abundance of microbial pharmacogenomics markers in relation to the antibiotics-treatable condition.

7. The system of claim 1, wherein the features comprise a nucleotide-associated functional feature associated with at least one of resistance and metabolization of a biologically active molecule, including at least one of the following: structural RNAs, regulatory RNAs, messenger RNAs, proteins and peptides.

8. The system of claim 1, wherein the antibiotics-treatable condition comprises at least one of a urinary tract infection and a sexually transmitted disease, and wherein the microbiome characterization system is operable to transform the supplementary data and the features extracted from the microbiome pharmacogenomics data and the at least one of the microbiome composition data and the microbiome functional diversity data into the characterization model for the at least one of the urinary tract infection and the sexually transmitted disease.

9. The system of claim 8, wherein the antibiotics-treatable condition comprises a gonorrhea-associated condition, and wherein the features comprise a microbiome pharmacogenomics feature extracted from the microbiome pharmacogenomics data and associated with a mosaic penA allele.

10. The system of claim 9, wherein the treatment system is operable to evaluate an efficacy of a cephalosporin treatment based on the microbiome pharmacogenomics feature, wherein the treatment system is operable to provide the treatment based on the efficacy.

11. The system of claim 1, further comprising an interface operable to improve display of antibiotics-related information associated with the antibiotics-treatable condition and derived based on a comparison between a user microbiome pharmacogenomics profile for the user relative to a user group sharing a demographic characteristic.

12. A method for evaluating an antibiotics-associated condition in relation to a first user, the method comprising:

determining microbiome pharmacogenomics data based on microorganism sequences derived from samples from a set of subjects;

receiving a supplementary dataset informative of the antibiotics-associated condition for the set of subjects;

determining a first set of microbiome pharmacogenomics features based on the microbiome pharmacogenomics data and the supplementary dataset;

generating a characterization model associated with the antibiotics-associated condition based on the first set of microbiome pharmacogenomics features;

determining a characterization for the first user in relation to the antibiotics-associated condition based on the characterization model; and providing a therapy to the first user based on the characterization, wherein the therapy is associated with the antibiotics-associated condition.

13. The method of claim 12, wherein determining the microbiome pharmacogenomics data comprises:

determining the microorganism sequences based on amplifying nucleic acid material from the samples;

determining alignments of the microorganism sequences to a reference nucleic acid sequence set associated with the antibiotics-associated condition; and determining the microbiome pharmacogenomics data based on the alignments.

14. The method of claim 13, wherein amplifying the nucleic acid material comprises performing, with a bridge amplification substrate of a next generation sequencing platform, multiplex amplification with the nucleic acid material, and wherein determining the microbiome pharmacogenomics data comprises determining the microbiome pharmacogenomics data at a computing system operable to communicate with the next generation sequencing platform.

15. The method of claim 12, further comprising obtaining a microbiome pharmacogenomics feature-selection rule associated with a correlation between the first set of microbiome pharmacogenomics features and antibiotic efficacy in relation to the antibiotics-associated condition, wherein determining the first set of microbiome pharmacogenomics features comprises determining the first set of microbiome pharmacogenomics features based on evaluating the microbiome pharmacogenomics data against the microbiome pharmacogenomics feature-selection rule.

16. The method of claim 12, wherein the first set of microbiome pharmacogenomics features comprises a nucleotide-associated functional feature associated with at least one of resistance and metabolization of a biologically active molecule.

17. The method of claim 12, wherein the therapy is operable to facilitate modification of a microbiome pharmacogenomics profile of the first user, the method further comprising:

receiving a post-therapy sample from the first user;

determining an updated set of microbiome pharmacogenomics features based on the post-therapy sample;

determining an updated characterization for the first user in relation to the antibiotics-associated condition based on the characterization model and the updated set of microbiome pharmacogenomics features; and promoting a first updated therapy to the first user based on the updated characterization.

18. The method of claim 17, further comprising:

generating an updated antibiotic therapy model based on the updated characterization for the first user; and promoting an antibiotic therapy to a second user based on the updated antibiotic therapy model, the antibiotic therapy operable to modulate a microbiome composition of the second user.

19. The method of claim 18, further comprising: determining a second set of microbiome pharmacogenomics features for the second user based on a second user sample, wherein promoting the antibiotic therapy based on the updated antibiotic therapy model comprises determining the antibiotic therapy based on processing the second set of microbiome pharmacogenomics features with a decision tree model.

20. The method of claim 12, wherein generating the characterization model comprises generating the characterization model based on a microbiome feature set comprising the first set of microbiome pharmacogenomics features and at least one of a microbiome composition diversity feature and a microbiome functional diversity feature, and wherein determining the characterization for the first user comprises determining the characterization for the first user based on a user microbiome feature set comprising a user microbiome pharmacogenomics feature and at least one of a user microbiome composition diversity feature and a user microbiome functional diversity feature.

21. The method of claim 20, wherein the antibiotics-associated condition comprises a gonorrhea-associated condition, wherein the microbiome composition diversity feature comprises a composition feature for a taxon associated with the gonorrhea-associated condition, and wherein the first set of microbiome pharmacogenomics features comprises a point mutation feature set for genes associated with the taxon.

22. The method of claim 21, wherein the point mutation feature set is associated with point mutations in at least one of a gyrA gene and a parC gene for the taxon.

* * * * *